(12) United States Patent
Brisben et al.

(10) Patent No.: US 11,052,255 B2
(45) Date of Patent: Jul. 6, 2021

(54) AUTO-THRESHOLD TEST FOR HIS-BUNDLE PACING

(71) Applicant: Cardiac Pacemakers, Inc., St. Paul, MN (US)

(72) Inventors: Amy Jean Brisben, Saint Paul, MN (US); David J. Ternes, Roseville, MN (US); Allan Charles Shuros, St. Paul, MN (US); Deepa Mahajan, North Oaks, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 65 days.

(21) Appl. No.: 16/256,746

(22) Filed: Jan. 24, 2019

(65) Prior Publication Data

US 2019/0275329 A1 Sep. 12, 2019

Related U.S. Application Data

(60) Provisional application No. 62/639,113, filed on Mar. 6, 2018.

(51) Int. Cl.
*A61N 1/368* (2006.01)
*A61N 1/362* (2006.01)
(Continued)

(52) U.S. Cl.
CPC ......... *A61N 1/3684* (2013.01); *A61N 1/0573* (2013.01); *A61N 1/3621* (2013.01);
(Continued)

(58) Field of Classification Search
CPC .... A61N 1/3684; A61N 1/371; A61N 1/0573; A61N 1/3682; A61N 1/3621;
(Continued)

(56) References Cited

U.S. PATENT DOCUMENTS 8,565,880 B2 10/2013 Dong et al.
8,688,216 B2 4/2014 Yost et al.
(Continued)

FOREIGN PATENT DOCUMENTS

EP 3431135 A1 1/2019
WO WO-2019173003 A1 9/2019

OTHER PUBLICATIONS

Sharma, Parikshit S., et al., "Permanent His Bundle Pacing as an Alternative to Biventricular Pacing for Cardiac Resynchronization Therapy: A Multi-Center Experience", Heart Rhythm Manuscript, Reference HRTHM 7347, DOI: 10.1016/j.hrthm.2017.10.014, 29 pages.

(Continued)

*Primary Examiner* — Gary Jackson
*Assistant Examiner* — Sebastian X Lukjan
(74) *Attorney, Agent, or Firm* — Schwegman Lundberg & Woessner, P.A.

(57) ABSTRACT

Systems and methods for pacing cardiac conductive tissue are described. A medical system includes an electrostimulation circuit to generate His-bundle pacing (HBP) pulses. A sensing circuit senses a physiologic signal, and detect a local His-bundle activation discrete from a pacing artifact of the HBP pulse. A control circuit verifies capture status in response to the HBP pulses. Based on the capture status, the control circuit determines one or more pacing thresholds including a selective HBP threshold representing a threshold strength to capture only the His bundle but not the local myocardium, and a non-selective HBP threshold representing a threshold strength to capture both the His bundle and the local myocardium. The electrostimulation circuit may deliver HBP pulses based on the selective and non-selective HBP thresholds.

20 Claims, 7 Drawing Sheets

(51) Int. Cl.
*A61N 1/05* (2006.01)
*A61N 1/37* (2006.01)
*A61N 1/36* (2006.01)
*A61B 5/349* (2021.01)

(52) U.S. Cl.
CPC .......... *A61N 1/3682* (2013.01); *A61N 1/371* (2013.01); *A61B 5/349* (2021.01); *A61N 1/0568* (2013.01); *A61N 1/36114* (2013.01); *A61N 1/36139* (2013.01); *A61N 1/3706* (2013.01)

(58) Field of Classification Search
CPC .............. A61N 1/3639; A61N 1/36139; A61N 1/36114; A61N 1/0568; A61N 1/3706; A61B 5/0452
See application file for complete search history.

(56) References Cited

U.S. PATENT DOCUMENTS

| | | |
|---|---|---|
| 8,688,234 B2 | 4/2014 | Ortega et al. |
| 2008/0319501 A1 | 12/2008 | Zhu et al. |
| 2009/0259272 A1* | 10/2009 | Reddy .................. A61N 1/0573 607/28 |
| 2011/0264158 A1* | 10/2011 | Dong .................. A61B 5/7264 607/9 |
| 2014/0107724 A1 | 4/2014 | Shuros et al. |

OTHER PUBLICATIONS

Shuros, Allan Charles, et al., "System and Methods for Correcting Cardiac Conduction Abnormality Using HIS-Bundle Pacing", U.S. Appl. No. 62/595,541, filed Dec. 6, 2017.

Vijayaraman, Pugazhendr, et al., "Permanent His Bundle Pacing (HBP): Recommendations From a Multi-Center HBP Collaborative Working Group for Standardization of Definitions, Implant Measuremenrs and Follow-Up", Heart Rhythm Manuscript, (https://doi.org/10.1016/j.hrthm.2017.10.039), 37 pages.

"International Application Serial No. PCT/US2019/014923, International Search Report dated Apr. 24, 2019", 4 pgs.

"International Application Serial No. PCT/US2019/014923, Written Opinion dated Apr. 24, 2019", 6 pgs.

* cited by examiner

AUTO-THRESHOLD TEST FOR HIS-BUNDLE PACING

CLAIM OF PRIORITY

This application claims the benefit of priority under 35 U.S.C. § 119(e) of U.S. Provisional Patent Application Ser. No. 62/639,113, filed on Mar. 6, 2018, which is herein incorporated by reference in its entirety.

TECHNICAL FIELD

This document relates generally to medical systems, and more particularly, to systems, devices and methods for pacing of cardiac conductive tissue, such as a His bundle.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways known as His-Purkinje system to various regions of the heart to excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction and/or deteriorated myocardium may cause dyssynchronous contraction of the heart, resulting in poor hemodynamic performance, including a diminished blood supply to the heart and the rest of the body. For example, an abnormal delay in the transmission of the action potentials in the His bundle can cause irregular or dyssynchronous contractions of the ventricles, resulting in an abnormal rhythm of the heart.

Artificial cardiac pacing system have been used to rectify cardiac dyssynchrony and to improve hemodynamic performance. The artificial cardiac pacing system can provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apex pacing directly excites the ventricular myocardium, rather than propagating the action potentials through the natural conduction pathways. Studies have shown that, in some patients, long-term RV apex pacing may result in loss of synchronous mechanical contraction of RV and LV, partially due to the interventricular delay in impulse propagation to the left ventricle. Consequently, permanent changes in myocardial perfusion and structure may develop over time in these patients, which may further decrease cardiac output and deteriorate ventricular function. BiV pacing involves RV pacing via one lead, and LV pacing via another lead, and has been demonstrated to restore substantially simultaneous contraction of both ventricles. However, the potential adverse impact on ventricular function produced by the RV apex pacing may still exist in BiV pacing. Additionally, compared to cardiac depolarization through AV node activation and propagation through the natural conduction pathways, the BiV pacing may not produce similarly coordinated cardiac contractions. Moreover, the surgical procedure for placing the LV lead through the coronary sinus and into a vein on the left ventricular wall can be complex and challenging in some patients.

OVERVIEW

Hemodynamic response to artificial pacing can depend on many factors, including pacing site selection and pacing configurations. Many patients receiving artificial pacing therapy have an intact His bundle and the natural cardiac electrical conduction system in the ventricles, and therefore having normal ventricular activation. Conventional cardiac pacing such as long-term RV apex pacing may cause a decrease in cardiac efficiency due to the uncoordinated contraction sequence, and eventually exhibit adverse long-term effects. Dyssynchronous contraction of the ventricles occurs during conventional pacing because the propagation of the activation sequence can be much slower when it occurs through working myocardium versus activation through the natural conduction system of the heart. The cells of the natural conduction system can propagate an activation signal about four times faster than working myocardium. A cardiac rhythm or functional management device configured to pace the His bundle is an alternative to conventional ventricular pacing. His-bundle pacing (HBP) may activate the heart's natural His-Purkinje system in some patients, and produce efficient and coordinated cardiac contractions. The potentially long-term harmful hemodynamic effects that may occur from continuous RV apex pacing may also be reduced.

However, when not being used effectively, HBP may not adequately restore cardiac synchrony. In some instances, the electrical stimulation fails to activate the His bundle, but only activates the para-Hisian myocardium surrounding the His bundle. Stimulating muscles near the His bundle may cause dyssynchronous patterns similar to RV apical pacing. This undesirable effect is referred to para-Hisian capture. There is an unmet need for an artificial pacing system that can produce desirable therapeutic effects of synchronous ventricular contraction via HBP, while reducing or eliminating unintended activation of non-targeted portions of the heart, such as the para-Hisian myocardium.

HBP pulses that capture the His-bundle fibers may sometimes concurrently activate other tissue near the His-bundle fibers, resulting in different capture patterns. A selective His-bundle capture (hereinafter referred to as "S-capture") results when HBP pulses activate only the His bundle without directly activating the adjacent working para-Hisian myocardium. If HBP pulses directly activate both the His bundle and the adjacent working myocardium, a non-selective His-bundle capture (hereinafter referred to as "NS-capture") occurs. Both S-capture and NS-capture activate viable His-bundle fibers and produce propagation of action potentials through the natural conduction system, thereby reducing long-term harmful hemodynamic effect. Because the ventricular activation and contraction during NS-capture is vastly dominated by rapidly conducting His-Purkinje system (including His bundle, bundle branches, and Purkinje fibers) as opposed to relatively slower muscle-to-muscle conduction, NS-capture can be as effective as S-capture in restoring or improving cardiac synchrony. However, S-capture is a more physiological capture status as it resembles intrinsic cardiac electrical and mechanical activation pattern without directly activating para-Hisian myocardium, and thus may be a preferred status over NS-capture in some patients. Additionally, S-capture may be more energy-efficient than NS-capture. A capture threshold represents minimum energy (e.g., stimulation voltage or current) required to activate excitable tissue such as His bundle fibers. Typically, selective HBP threshold (hereinafter referred to as "S-threshold") is lower than non-selective HBP threshold (hereinafter referred to as "NS-threshold"). HBP pulses that produce S-captures generally consumes less power that HBP pulses that produce NS-captures. As a result, energy saving and extended device longevity may be achieved with S-capture. However, HBP pulses having stimulation strength close to the S-threshold may be more prone to loss of capture than HBP pulses having stimulation strength close to the higher NS-threshold. Additionally, the energy-saving benefit associated with S-capture may also depend on S-threshold value relative to NS-threshold value. To ensure effective capture, pacing output may be set to the pacing threshold plus a safety margin. If S-threshold and NS-threshold are close enough (e.g., lower than the safety margin), then the pacing output, when set to S-threshold plus the safety margin, is likely to exceed the NS-threshold and produce NS-capture. If S-threshold and NS-threshold are well separated (e.g., substantially greater than the specified safety margin), then the pacing output, when set to S-threshold plus the safety margin, is likely to be less than the NS-threshold and produce S-capture.

Pacing threshold, such as S-threshold or NS-threshold, may be different from person to person. For a patient, pacing threshold may vary over time, such as due to changes in patient pathophysiology (e.g., development of a new medical condition such as myocardial ischemia, or progression of an existing medical condition), medication, or lead migration, dislodgment, or micro-dislodgment, among other causes. Determining pacing threshold and tracking changes of that threshold over time in a patient can be beneficial to program individualized pacing therapy to achieve desired patient outcome. For example, based on relative strength of S-threshold value and the NS-threshold value and among other factors, some patients are decided to be more suitable for HBP with S-capture, while some other patients may be more suitable for HBP with NS-capture. The present inventors have recognized a need of a computerized HBP system that may automatically determine or adjust patient-specific S-threshold and NS-threshold, and to deliver HBP in accordance with the determined S-threshold and NS-threshold to achieve desired capture status and patient outcome.

Embodiments of the present subject matter provide systems, devices, and methods for pacing cardiac conductive tissue, such as a His bundle. An exemplary medical system includes circuitry for delivering HBP pulses to stimulate a His bundle, and detecting a local His-bundle activation from a physiologic signal in response to HBP delivery. The HBP pulses may be programmed to have each of a number of stimulation strength values. The local His-bundle activation is discrete from a pacing artifact of the HBP pulse. Using the sensed local His-bundle activation, a control circuit may verify a capture status as one of capture types including S-capture, NS-capture, a para-Hisian capture, or a loss of capture. The control circuit may determine one or more of pacing thresholds, including an S-threshold and an NS-threshold, based on the verified capture status. The S-threshold represents a threshold strength for an HBP pulse to capture only the His bundle but not the local myocardium at the pacing site. The NS-threshold represents a threshold strength for an HBP pulse to capture both the His bundle and the local myocardium. The electrostimulation circuit may deliver HBP pulses according to stimulation strength determined based on the S-threshold and/or the NS-threshold.

Example 1 is a system for pacing a heart. The system comprises an electrostimulation circuit configured to generate His-bundle pacing (HBP) pulses having a stimulation strength to stimulate a His bundle of the heart, a sensing circuit configured to sense a physiologic signal and to detect, from the sensed physiologic signal, a local His-bundle activation discrete from a pacing artifact of the delivered HBP pulses, and a control circuit. The control circuit may be configured to verify a capture status using the detection of the local His-bundle activation, and determine, using the verification of the capture status, one or more of (1) a selective HBP threshold (S-threshold) representing a threshold strength for the HBP pulses to capture only the His bundle but not local myocardium, or (2) a non-selective HBP threshold (NS-threshold) representing a threshold strength for the HBP pulses to capture both the His bundle and the local myocardium.

In Example 2, the subject matter of Example 1 optionally includes the sensing circuit that may be configured to detect an isoelectric interval that separates the local His-bundle activation from the pacing artifact of the HBP pulse. The control circuit may be configured to verify the capture status further using the detected isoelectric interval.

In Example 3, the subject matter of any one or more of Examples 1-2 optionally includes the control circuit that may be configured to verify the capture status at a specific stimulation strength using a plurality of detected local His-bundle activations in response to a plurality of HBP pulses having the specific stimulation strength.

In Example 4, the subject matter of any one or more of Examples 1-3 optionally includes the sensing circuit that may be configured to sense the physiologic signal including a His-bundle electrogram, and detect the local His-bundle activation using an amplitude or a morphology of the sensed His-bundle electrogram.

In Example 5, the subject matter of any one or more of Examples 1-4 optionally includes the control circuit that may be configured to verify the capture status, including determining the capture status as one of a selective His-bundle capture (S-capture) status if the local His-bundle activation is present, a non-selective His-bundle capture (NS-capture) status if the local His-bundle activation is absent, or a loss of capture (LOC) status indicative of a capture of neither the His bundle nor the local myocardium. The S-capture status represents a capture of only the His bundle but not the local myocardium, and the NS-capture status represents a capture of both the His bundle and the local myocardium.

In Example 6, the subject matter of Example 5 optionally includes the control circuit that may be configured to ramp up the stimulation strength from a first initial stimulation strength, and determine the NS-threshold corresponding to a transition from an S-capture status to an NS-capture status in response to HBP pulses delivered according to the ramp-up of the stimulation strength.

In Example 7, the subject matter of Example 6 optionally includes the control circuit that may be configured to ramp up the stimulation strength, and determine the S-threshold corresponding to a transition from an LOC status to an S-capture status in response to HBP pulses delivered according to the ramp-up of the stimulation strength.

In Example 8, the subject matter of Example 5 optionally includes the control circuit that may be configured to ramp down the stimulation strength from a second initial stimulation strength, and determine the NS-threshold corresponding to a transition from an NS-capture status to an S-capture status in response to HBP pulses delivered according to the ramp-down of the stimulation strength.

In Example 9, the subject matter of Example 8 optionally includes the control circuit that may be configured to ramp down the stimulation strength, and determine an S-threshold corresponding to a transition from an S-capture status to an LOC status in response to HBP pulses delivered according to the ramp-down of the stimulation strength.

In Example 10, the subject matter of any one or more of Examples 1-9 optionally includes the control circuit that may be configured to verify the capture status including determining the capture status as one of (1) a selective His-bundle capture with conduction abnormality correction (Sc-capture), or (2) a selective His-bundle capture without conduction abnormality correction (Sn-capture), and determine a selective HBP threshold with conduction abnormality correction (Sc-threshold) based on at least the verification of the Sc-capture status or the Sn-capture status.

In Example 11, the subject matter of Example 10 optionally includes the control circuit that may be configured to: ramp up the stimulation strength and determine the Sc-threshold corresponding to a transition from an Sn-capture status to an Sc-capture status in response to HBP pulses delivered according to the ramp-up of the stimulation strength; or ramp down the stimulation strength and determine the Sc-threshold corresponding to a transition from an Sc-capture status to an Sn-capture status in response to HBP pulses delivered according to the ramp-down of the stimulation strength.

In Example 12, the subject matter of any one or more of Examples 5-11 optionally includes the sensing circuit that may be further configured to sense a far-field cardiac electrical signal, and the control circuit that may be configured to verify the capture status further using the sensed far-field cardiac electrical signal.

In Example 13, the subject matter of Example 12 optionally includes the sensing circuit that may be configured to extract a morphologic feature of the far-field cardiac electrical signal, and the control circuit that may be configured to, in response to the extracted morphologic feature satisfying a specified condition, determine an NS-threshold corresponding to (1) a transition from an S-capture status to an NS-capture status in response to HBP pulses delivered according to a ramp-up of the stimulation strength, or (2) a transition from an NS-capture status to an S-capture status in response to HBP pulses delivered according to a ramp-down of the stimulation strength.

In Example 14, the subject matter of any one or more of Examples 5-13 optionally includes the electrostimulation circuit that may be configured to generate the HBP pulses having stimulation strength above the determined NS-threshold, and the control circuit that may be configured to, in response to a verification of S-capture status, increment the stimulation strength until an NS-capture status is verified.

In Example 15, the subject matter of any one or more of Examples 5-13 optionally includes the electrostimulation circuit that may be configured to generate the HBP pulses having stimulation strength above the determined S-threshold and below the determined NS-threshold, and the control circuit that may be configured to: in response to a verification of an NS-capture status, decrement the stimulation strength until an S-capture status is verified; and in response to a verification of a loss of capture status, increment the stimulation strength until an S-capture status is verified.

Example 16 is a method for operating a pacing system to stimulate a heart. The method comprises steps of: generating, via an electrostimulation circuit, His-bundle pacing (HBP) pulses to stimulate a His bundle of the heart, the HBP pulses having a stimulation strength; sensing, via a sensing circuit, a physiologic signal and determining a presence of a local His-bundle activation discrete from a pacing artifact of the delivered HBP pulse via a sensing circuit; verifying, via a control circuit, a capture status using the sensed local His-bundle activation; and determining, using the verification of the capture status, one or more of a selective HBP threshold (S-threshold) or a non-selective HBP threshold (NS-threshold) via the control circuit, the S-threshold representing a threshold strength for the HBP pulses to capture only the His bundle but not local myocardium, the NS-threshold representing a threshold strength for the HBP pulses to capture both the His bundle and the local myocardium.

In Example 17, the subject matter of Example 16 optionally includes verifying the capture status by determining the capture status as one of: a selective His-bundle capture (S-capture) status if the local His-bundle activation is present; a non-selective His-bundle capture (NS-capture) status if the local His-bundle activation is absent; or a loss of capture (LOC) status indicative of a capture of neither the His bundle nor the local myocardium. The S-capture status represents a capture of only the His bundle but not the local myocardium, and the NS-capture status represents a capture of both the His bundle and the local myocardium.

In Example 18, the subject matter of Example 17 optionally includes determining the one or more of the S-threshold or the NS-threshold by performing one of ramping up the stimulation strength and determining the NS-threshold corresponding to a transition from an S-capture status to an NS-capture status in response to HBP pulses delivered according to the ramp-up of the stimulation strength, or ramping down the stimulation strength and determining the NS-threshold corresponding to a transition from an NS-capture status to an S-capture status in response to HBP pulses delivered according to the ramp-down of the stimulation strength.

In Example 19, the subject matter of any one or more of Examples 17-18 optionally includes determining the one or more of the S-threshold or the NS-threshold by performing one of ramping up the stimulation strength and determining the S-threshold corresponding to a transition from an LOC status to an S-capture status in response to HBP pulses delivered according to the ramp-up of the stimulation strength, or ramping down the stimulation strength and determining the S-threshold corresponding to a transition from an S-capture status to an LOC status in response to HBP pulses delivered according to the ramp-down of the stimulation strength.

In Example 20, the subject matter of any one or more of Examples 16-19 optionally includes verifying the capture status as one of (1) a selective His-bundle capture with conduction abnormality correction (Sc-capture), or (2) a selective His-bundle capture without conduction abnormality correction (Sn-capture), and determining a selective HBP threshold with conduction abnormality correction (Sc-threshold) based on at least the verification of the Sc-capture status or the Sn-capture status.

In Example 21, the subject matter of Example 20 optionally includes determining the Sc-threshold by performing at least one of ramping up the stimulation strength and determining the Sc-threshold corresponding to a transition from an Sn-capture status to an Sc-capture status in response to HBP pulses delivered according to the ramp-up of the stimulation strength, or ramping down the stimulation strength and determining the Sc-threshold corresponding to a transition from an Sc-capture status to an Sn-capture status in response to HBP pulses delivered according to the ramp-down of the stimulation strength.

In Example 22, the subject matter of any one or more of Examples 16-21 optionally includes sensing a far-field cardiac electrical signal, verifying the capture status further using the sensed far-field cardiac electrical signal, and in response to the far-field cardiac electrical signal satisfying a specified condition, determining an NS-threshold corresponding to (1) a transition from an S-capture status to an NS-capture status in response to HBP pulses delivered according to a ramp-up of the stimulation strength, or (2) a transition from an NS-capture status to an S-capture status in response to HBP pulses delivered according to a ramp-down of the stimulation strength.

The systems, devices, and methods discussed in this document may improve the technology of cardiac pacing in patients with cardiac disease, such as heart failure. HBP may activate natural His-Purkinje system, thereby preserving ventricular synchrony and improving cardiac performance without structural and functional impairment to the heart. A technological challenge in HBP is to determine appropriate, individualized, stimulation output (e.g., stimulation strength) to ensure His-bundle capture and activation of the His-Purkinje system. While a high stimulation output may more likely to produce His-bundle capture, it consumes more battery power, and may have side effects in some patients, such as phrenic nerve stimulation, pain sensation, among others. Between S-capture and NS-capture, the potential extra benefit of S-capture may vary among patients. The present subject matter provides a technical solution to the challenge of individualized HBP therapy, which involves testing and determination of patient-specific S-threshold and NS-threshold, and programming individualized HBP based on the S-threshold and NS-threshold. The individualized stimulation output as discussed in this document may improve cardiac pacing technology, particularly individualized therapy, with little to no additional cost or system complexity. The His-bundle pacing as discussed in the present document may improve pacing efficiency utilizing the natural conduction mechanisms of the heart, while reducing long-term harmful hemodynamic effects associated with RV apex pacing. With improved synchrony and cardiac performance, fewer unnecessary medical interventions, such as drugs, procedures, or device therapies, may be scheduled, prescribed, or provided to such patients. As a result, overall system cost savings may be realized.

The HBP guided by individualized pacing thresholds such as S-threshold and NS-threshold as discussed in this document may also improve the functionality of a cardiac pacing system or device. Device memory usage may be more efficient by storing various HBP thresholds, such as S-threshold and NS-threshold, which are clinically more relevant to titrating cardiac pacing therapy to improve therapy efficacy. As discussed above, S-capture may be more physiological and have power benefit over NS-capture, but may be prone to loss of capture. NS-capture is not as physiological, but has a wider margin to avoid loss of capture. By identifying patients that are suitable for HBP with S-capture, battery life and implantable device longevity may be extended, unnecessary device therapies can be avoided, or device size may be reduced to achieve existing performance metrics.

While His-bundle pacing is specifically discussed in this document, this is meant only by way of example and not limitation. It is within the contemplation of the inventors, and within the scope of this document, that the systems, devices, and methods discussed herein may be applied to stimulate other conductive cardiac tissue, such as the right or left bundle branches or fascicles, or the Purkinje fibers.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for pacing cardiac conductive tissue. An embodiment of the system may include an electrostimulator to generate His-bundle pacing (HBP) pulses to stimulate a His bundle. The system may sense a physiologic signal, and detect a local His-bundle activation discrete from a pacing artifact of the HBP pulse. A control circuit verifies capture status in response to the HBP pulses having different stimulation strength values. Based on the capture status, the control circuit determines one or more pacing thresholds, including an S-threshold and an NS-threshold. The electrostimulation circuit delivers HBP pulses according to the stimulation strength determined based on the selective and non-selective HBP thresholds.

Figure 1:
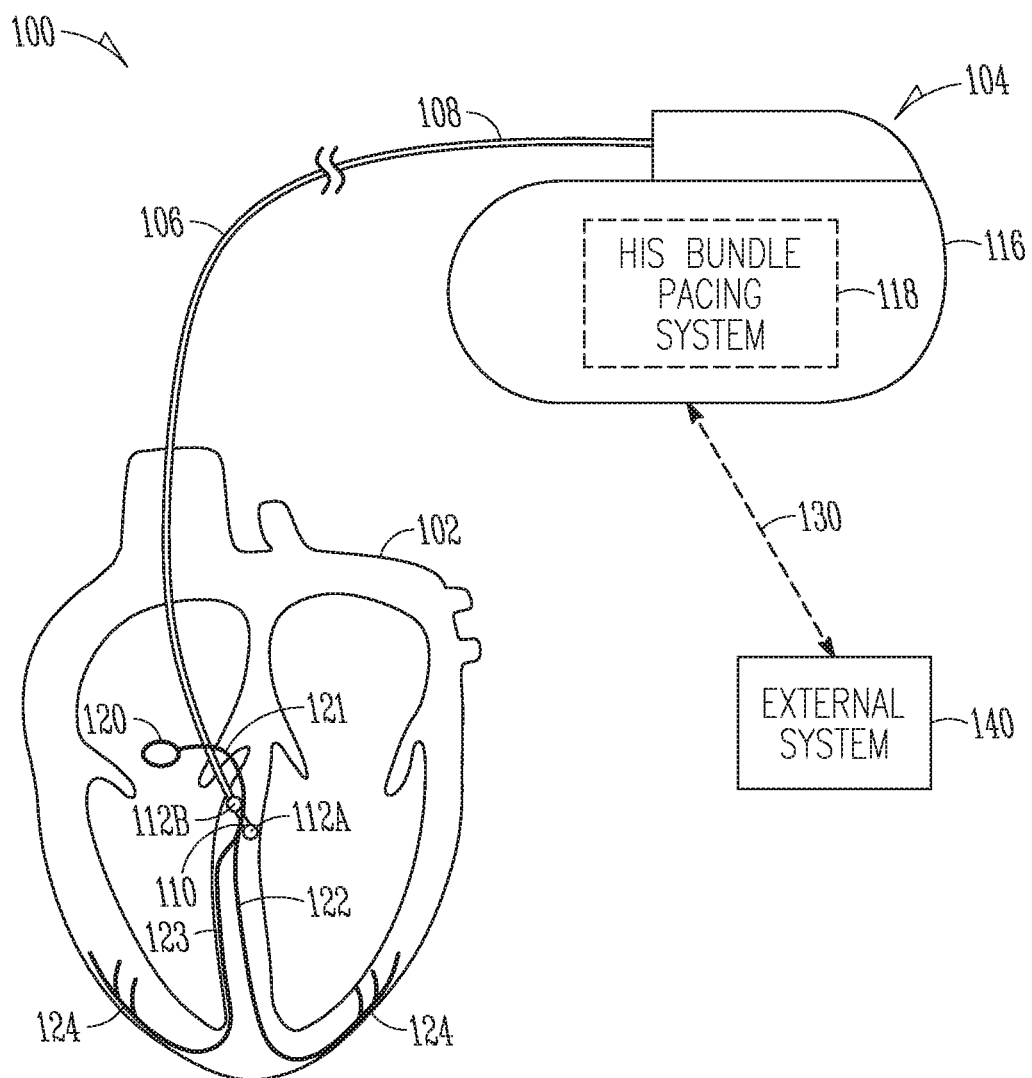
FIG. 1 illustrates generally an example of a cardiac disease management system and portions of an environment in which the system may operate.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG. 1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-112B, are positioned in or on a His bundle 121, a region distal to the blocked or slowly conducting AV node and in the AV septum, an interventricular septum region, or a right atrial region near the His-bundle 121. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-112B, are positioned at or near other parts of the natural conduction pathways, such as one of the bundle branches 122 or 123, the Purkinje fibers 124, or other conductive tissue, in addition to or in lieu of a region at or near the His bundle 121.

In an example, the lead 106 may be a single pass lead having a plurality electrodes for stimulating multiple cardiac sites, including electrodes disposed at or near the His bundle (e.g., the electrodes 112A-112B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. In various examples, the cardiac disease management system 100 may include one or more leadless stimulators/sensors untethered to a lead and in wireless communication with the IMD 104. The leadless stimulators/sensors may deliver electrostimulation, sense a physiological signal, such as cardiac electrical signals in response to cardiac stimulation, and transmit the sensed data to the IMD 104.

The IMD 104 may include a hermetically sealed housing 116 that houses one or more of an electrostimulation circuit, a sensing circuit, a control circuit, a communication circuit, and a battery, among other components. In an example, the IMD 104 includes a His-bundle pacing system 118 configured to generate His-bundle pacing (HBP) pulses to stimulate the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-112B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or bipolar His-bundle pacing may be selected by a system user from a plurality of candidate electrodes from one or more leads of the lead system, and programmed into the His-bundle pacing system 118. In some examples, HBP pulses may be provide by a leadless device, such as a leadless cardiac pacemakers (LCP). One or more electrodes may be distributed on the body of the LCP and in contact with His-bundle region to deliver the HBP pulses.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, a thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others.

The His-bundle pacing system 118 may sense a cardiac electrical or mechanical signal in response to the delivery of HBP pulses using one or more electrodes or physiologic sensors. In an example, the His-bundle pacing system 118 may sense a physiologic signal in response to the HBP pulses, such as a local His-bundle EGM using one or more of the electrodes 112A and 112B, and detect therefrom a local His-bundle activation discrete from a pacing artifact of the HBP pulse. In various examples, the His-bundle pacing system 118 may sense a far-field cardiac electrical signal from the His bundle or an atrium. The far-field signal is representative of ventricular contractions. The His-bundle pacing system 118 may use the sensed signals to verify His-bundle capture status, such as one of a selective His-bundle capture ("S-capture") or a non-selective His-bundle capture ("NS-capture"). An S-capture occurs if the HBP activates only the His bundle without directly activating the adjacent working myocardium. An NS-capture occurs if the HBP directly activates both the His bundle and the adjacent working myocardium. Based on the verification of the capture status, the His-bundle pacing system 118 may determine one or more HBP thresholds, such as a selective HBP threshold ("S-threshold") representing a threshold strength for HBP pulses to capture only the His bundle but not local myocardium, or a non-selective HBP threshold ("NS-threshold") representing a threshold strength for HBP pulses to capture both the His bundle and the local myocardium. The His-bundle pacing system 118 may deliver HBP pulses according to stimulation strength determined based on the S-threshold and/or the NS-threshold.

The IMD 104 may be configured to communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display received information to the user, and receive user input for operation control of the IMD 104. In an example, the external system 140 may be configured to verify pacing capture status, perform pacing threshold test to determine one or more HBP thresholds (e.g., NS-threshold and S-threshold). The capture verification and threshold testing may be executed periodically, or triggered by a specific event such as a user command. A user may use the external system 140 to program the IMD 104, such as to configure a pacing vector (e.g., specifying anode and cathode electrodes) to deliver HBP, or to configure a sense vector to sense a physiological signal.

The external system 140 may include a remote device in a location relatively distant from the IMD 104 and in communication with the proximal external device via a telecommunication network. The remote device can evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, capture verification, or classification of capture types, among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
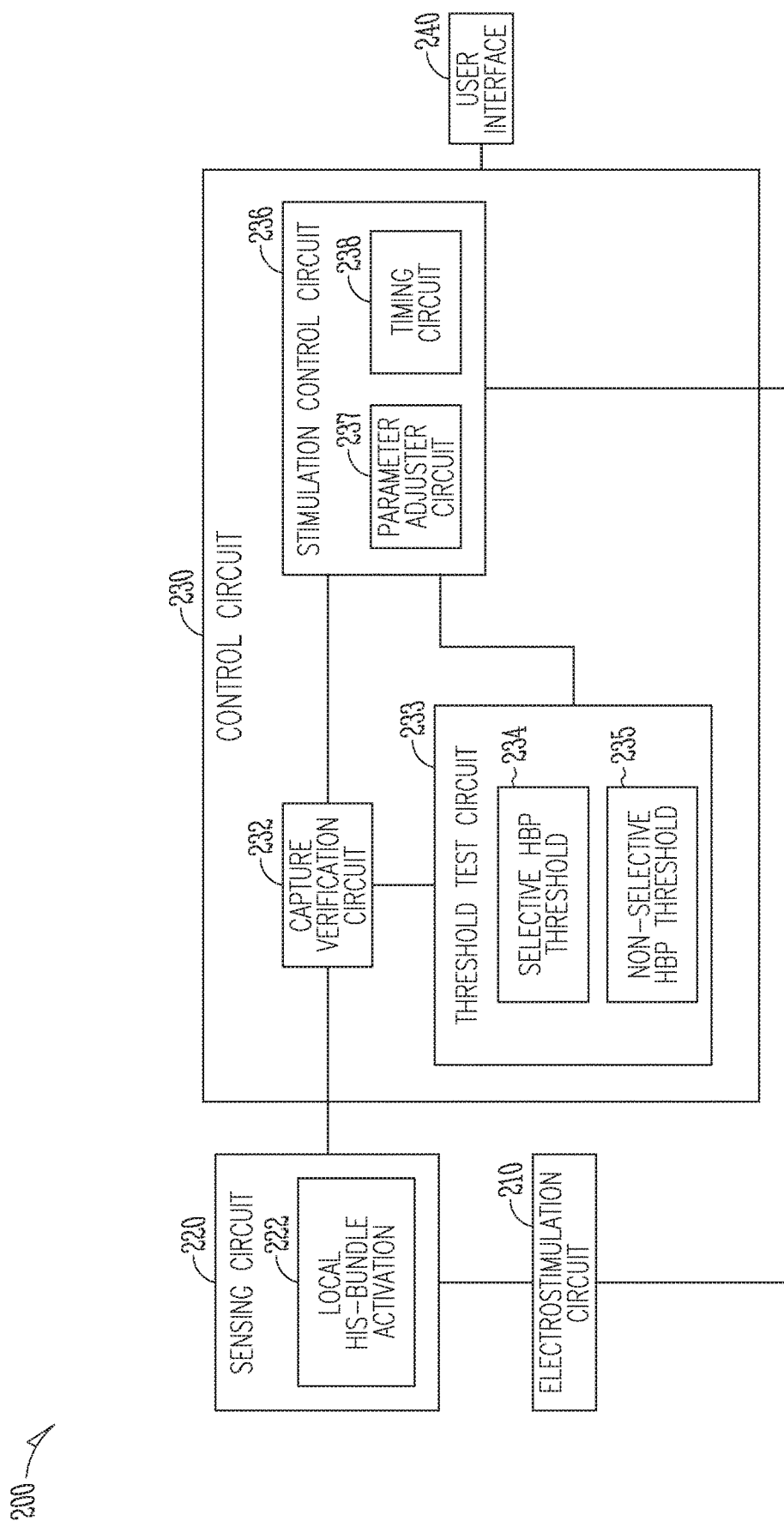
FIG. 2 is a block diagram illustrating an example of portions of a His-bundle pacing system.

FIG. 2 is a block diagram illustrating an embodiment of portions of a His-bundle pacing system 200. The His-bundle pacing system 200 represents an embodiment of the His-bundle pacing system 118, and may include an electrostimulation circuit 210, a sensing circuit 220, a control circuit 230, and a user interface 240.

The electrostimulation circuit 210 may be configured to generate stimulation energy for delivery to the heart 102, such as via one or more leads and the associated electrodes. The electrostimulation circuit 210 may be configured to generate His-bundle pacing (HBP) pulses for delivery to a target site at or near the His bundle such as via the lead 106 and one or more of the electrodes 112A-112B. The target site may include an interventricular septum region or a right atrial region near the His-bundle, or other conductive tissue such as right or left bundle branches or fascicles, or Purkinje fibers. In an example, the HBP pulses may be delivered in multiple cardiac cycles, such that at least one pulse is delivered within each of the multiple cardiac cycles. In various examples, the electrostimulation circuit 210 may additionally generate electrostimulation to stimulate non-cardiac tissue, such as nerve tissue, muscle tissue, or other excitable tissue.

The electrostimulation circuit 210 may generate HBP pulses according to one or more stimulation parameters, such as provided by control circuit 230. Examples of the stimulation parameters may include information about stimulation site, stimulation strength, stimulation mode, or stimulation timing, among other parameters. Stimulation site includes information about pacing site, pacing vector configuration (e.g., anode and cathode electrodes), unipolar or bipolar pacing, cardiac resynchronization therapy (CRT), BiV pacing, or synchronized left ventricle (LV)-only pacing, single site pacing of only one site of a heart chamber (e.g., the left ventricle), or multisite pacing (MSP) of two or more sites of a heart chamber within the same cardiac cycle, among others. Stimulation strength parameters determine the amount of energy delivered to the pacing site, and may include pulse amplitude, pulse width, pulse frequency, pulse waveform, duty cycle, or stimulation duration.

Stimulation mode includes, by way of example and not limitation, an atrial-Hisian (AH) pacing mode, a His-ventricular (HV) pacing mode, or an atrial-His-ventricular (AHV) pacing mode. In the AH pacing mode, the HBP pulses may be delivered only when intrinsic atrial activation (As), or atrial pacing (Ap), fails to produce propagatable depolarization of the AV node and the His bundle. The AH pacing mode may be suitable for patients with varying degrees of heart block or sick sinus syndrome. The HV pacing mode involves sequential pacing of the His bundle and the ventricle. The ventricular pacing may be provided in a demand mode, such that the ventricular pacing pulses are delivered only when the His pacing fails to produce propagatable depolarization of the ventricles. The HV pacing mode may be indicated for patients with persistent or chronic atrial fibrillation, or patients treated with atrioventricular node ablation to slow and regularize ventricular rhythm. The AHV pacing mode involves sequential atrial, Hisian, and ventricular pacing. One or more of the His-bundle pacing or the ventricular pacing may be delivered in a demand mode. The AHV pacing mode may be indicated for patients with cardiac dyssynchrony and having received cardiac resynchronization therapy, patients suffering from heart failure with left bundle branch block, heart failure induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an As or an Ap event. An AH timing represents a latency period, within a cardiac cycle, from an intrinsic As event or an Ap event to the delivery of a HBP pulse. In demand HV pacing mode, the ventricular pacing pulses are timed relative to a His pacing event. An HV timing represents a latency period, within a cardiac cycle, from a His bundle event (e.g., a HBP pulse) to the delivery of ventricular pacing pulse. In an example, if an HBP pulse fails to induce ventricular depolarization, a backup ventricular pacing may be delivered at the end of the HV timing. The stimulation timing parameters may additionally include parameters associated with CRT or MSP therapy, such as atrial-ventricular delay (AVD) representing a latency period from an As or Ap event to ventricular pacing, an RV-LV interventricular pacing delay (VVD) representing a time delay between ventricular pacing at the left and right ventricles, or intra-ventricular pacing delay representing a time delay between pacing at multiple site of a ventricle.

The electrostimulation circuit 210 may be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP, selective HBP causes only the excitation (depolarization) of the His bundle, without direct excitation of para-Hisian myocardium adjacent to the His bundle. Non-selective HBP directly causes excitation of both the His bundle and the para-Hisian myocardium. If the HBP pulses cause only excitation of the para-Hisian myocardium or other unintended cardiac tissue, without direct excitation of the His-bundle fibers, then a para-Hisian pacing results. If no tissue excitation is induced by HBP (e.g., neither the para-Hisian myocardium capture nor the His-bundle capture), then a loss of capture (LOC) results.

The electrostimulation circuit 210 may be capable of generating backup pacing pulses for delivery to the heart to excite the myocardium and prevent asystole. The backup pacing pulses may be delivered when a loss of capture is produced, or alternatively when para-Hisian capture is produced. The backup pacing may be delivered to a target ventricular site via a lead with associated electrodes disposed in or on a ventricle, such as a right ventricle. Additionally or alternatively, the backup pacing may be delivered to the His bundle, such as the site for delivering HBP pulses, via the same His-bundle pacing lead with associated electrodes. In an example, the backup pacing may include high-output pacing (HOP) pulses with higher pacing energy than conventional pacing pulses. The HOP pulse may be a biphasic or multiphasic waveform. In an example, the HOP pulse may have a peak-to-peak voltage amplitude of 5-8 volts, and a pulse duration of 50-70 milliseconds (msec). With higher amount of energy delivered to the myocardium, the HOP pulse may increase myocardial contractility and improve systolic function. However, chronic HOP pacing may overstress the heart and potentially be hazardous in some heart failure patients. According, in some examples, the HOP pulses may be delivered on an intermittent basis, such that the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al. U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

The sensing circuit 220 may be coupled to one or more electrodes or physiologic sensors to sense a physiologic signal indicative of a response of a portion of the heart 102 to the delivery of HBP pulses. Examples of the sensed signals may include an electrocardiogram (ECG), an electrogram (EGM) of a portion of the heart such as atrial EGM, ventricular EGM, or evoked His potential, an impedance signal, a heart sound signal, or a pressure signal, among other physiological or hemodynamic signals indicative of a tissue response to the delivery of HBP pulses. The sensing circuit 220 may detect from the sensed signal a local His-bundle activation 222 discrete from a pacing artifact of the HBP pulse, such as using one or more of the electrodes 112A or 112B. The local His-bundle activation may be detected in a detection time window that begins at the HBP pulse delivery, and sustains for a specified duration. A local His-bundle activation is detected if the His-bundle EGM amplitude exceeds a specified threshold. Additionally or alternatively, the local His-bundle activation may be detected using signal morphology, such as based on a similarity metric between a His-bundle EGM morphology and a morphology template. In some examples, to improve detection reliability, the sensing circuit 220 may detect local His-bundle activation for a plurality of HBP pulses delivered over a number of cardiac cycles. A local His-bundle activation is determined to present if the His-bundle EGM consistently satisfies the amplitude or morphology detection conditions in response to the plurality of HBP pulses over a number of cardiac cycles.

In some examples, the sensing circuit 220 may additionally detect from the His-bundle EGM an isoelectric interval that separates the local His-bundle activation 222 from the pacing artifact of the HBP pulse. An isoelectric interval is a time interval between the HBP pacing artifact and the local His-bundle activation, during which the EGM maintains a baseline level. Presence of a local His-bundle activation and isoelectric interval in a His-bundle EGM may be indicative of a selective His-bundle capture by the HBP pulses. Examples of local His-bundle activation and isoelectric interval produced by HBP pulses are discussed below, such as with reference to FIG. 3.

In some examples, portions of the His-bundle pacing system 200 may be implemented distributedly between two devices. In an example, a first device may include the electrostimulation circuit 210 and a stimulation delivery system such as the lead and associated electrodes for delivering the HBP pulses, and a second device may include the sensing circuit 220 and at least a portion of the control circuit 230. The sensing circuit 220 of the second device may be configured to sense, among other signals, the far-field ventricular response to the HBP pulses. In an example, the first and second devices are both implantable devices. In another example, at least one of the first or the second device is a non-implantable, wearable device.

The control circuit 230 may be configured to verify that the HBP pulses capture one or more conductive tissue such as the His bundle or the myocardium, and control the delivery of HBP pulses based on the capture status. In an example, the control circuit 230 can be implemented as a part of a microprocessor circuit in the cardiac disease management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute instructions of performing the functions, methods, or techniques described herein.

As illustrated in FIG. 2, the control circuit 230 may include circuit sets comprising a capture verification circuit 232, a threshold test circuit 233, and a stimulation control circuit 236. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The capture verification circuit 232 is configured to determine His-bundle capture status using at least the local His-bundle activation 222. Capture verification may be carried out according to a specified schedule, such as on a periodic basis, or continuously on a beat-by-beat basis (i.e., verifying capture in response to each HBP pulse). In an example, the capture verification circuit 232 may determine an S-capture status if the local His-bundle activation is present, or an NS-capture status if the local His-bundle activation is absent. In another example, the capture verification circuit 232 may determine the His-bundle capture status further using the presence of an isoelectric interval between the local His-bundle activation 222 and the pacing artifact of the HBP pulse, such as detecting the His-bundle EGM amplitude (e.g., between the artifact of the HBP pulse and the local His-bundle activation) falling below an amplitude threshold. Presence of the isoelectric interval is more likely indicative of S-capture. During NS-capture, direct para-Hisian myocardium activation by the HBP pulses may result in ventricular fusion, producing pseudo-delta wave subsequent to the HBP pacing artifact. As a result, no isoelectric interval may be present in the case of NS-capture.

In various examples, to achieve a more reliable determination of capture status, the capture verification circuit 232 may detect the presence of local His-bundle activations over a number or cardiac cycles in response to a plurality of HBP pulses having the same stimulation strength. In an example, the capture verification circuit 232 determines that an S-capture has occurred if consecutive 3-5 local His-bundle activations are detected from the His-bundle EGM.

In various examples, the capture verification circuit 232 may determine other capture status in addition to the S-capture 234 and the NS-capture 235, such as a loss of capture (LOC), a para-Hisian capture, a partial capture, among others. An LOC is characterized by neither the para-Hisian myocardium capture nor the His-bundle capture. A para-Hisian capture refers to activation of only the para-Hisian myocardium without excitation of the His bundle directly caused by the delivery of HBP pulses. A partial capture refers to activation of a portion of the His-bundle fibers. The partial capture may occur in patients with intra-Hisian conduction abnormalities, such as bundle branch blocks. In an example, the capture verification circuit 232 may distinguish a first type of S-capture without conduction abnormality correction ("Sn-capture") from a second type of S-capture with conduction abnormality correction ("Sc-capture"), as to be discussed in the following with reference to FIG. 4. In various examples, the capture verification circuit 232 may detect His-bundle capture status using additional patient information, such as far-field cardiac electrical signals or patient hemodynamic information. Examples of capture verification based on various signal sources are discussed below, such as with reference to FIG. 4.

The threshold test circuit 233 may be configured to determine one or more HBP pacing thresholds, each representing minimal energy required to activate the His bundle with a particular capture status. By way of non-limiting example and as illustrated in FIG. 2, the HBP thresholds include a selective HBP threshold (S-threshold) 234 and a non-selective HBP threshold (NS-threshold) 235. The S-threshold 234 represents minimum energy (e.g., pulse amplitude) of HBP pulses to produce an S-capture status. The NS-threshold 235 represents minimum energy (e.g., pulse amplitude) of HBP pulses to produce an NS-capture status by HBP. The pacing threshold may be determined during implantation of the IMD 104, and updated periodically at specified time period, or triggered by a specific event (e.g., when HBP pulses fail to activate the His bundle) or by a user command.

The threshold test may involve delivering HBP pulses (e.g., via the electrostimulation circuit 210) at or near the His bundle in accordance with a threshold test protocol. The threshold test protocol can be instructions executable by a machine such as a microprocessor. The instructions specify programming a stimulation parameter to different values and measuring, for each programmed parameter value, a corresponding capture status. In various examples, the stimulation parameter, such as pulse amplitude, may be incremented following a ramp-up protocol, decremented following a ramp-down protocol, or sweep through a set of parameter values such as stored in a storage device. For each stimulation parameter value (e.g., pulse amplitude), the capture verification circuit 232 determines a capture status. As the stimulation parameter value is changed such as according to a ramp-up or ramp-down protocol, the threshold test circuit 233 may detect a transition from a first capture status to a second capture status of a different type, and determine a HBP threshold based on that detected transition of capture status.

The threshold test circuit 233 may determine an HBP threshold other than the S-threshold 234 and the NS-threshold 235. In an example, the threshold test circuit 233 may determine an HBP threshold associated with conduction abnormality correction. An example of such a threshold is a selective HBP threshold with conduction abnormality correction (Sc-threshold), which represents minimum energy (e.g., pulse amplitude) of HBP pulses required to correct the conduction abnormality and produce an Sc-capture. The threshold test circuit 233 may execute a threshold test protocol, and determine the Sc-threshold based on a detection of transition between Sc-capture and Sn-capture. Another example is a non-selective HBP threshold with conduction abnormality correction (NSc-threshold). The threshold test circuit 233 may execute a threshold test protocol, and determine the NSc-threshold based on a detection of transition between a first type of NS-capture without conduction abnormality correction ("NSn-capture") and a second type of NS-capture with conduction abnormality correction ("NSc-capture"). Examples of various HBP threshold test protocols are discussed below, such as with reference to FIG. 5.

The stimulation control circuit 236 may include a parameter adjuster circuit 237 configured to determine or update a stimulation parameter value based at least on one or more of the HBP thresholds, such as determined by the threshold test circuit 233. The stimulation parameter may be updated periodically at specified time period, or triggered by a specific event. The stimulation parameter may be updated automatically or manually by a user via a user interface 240. In an example, the parameter adjuster circuit 237 may set the HBP pulse amplitude to the NS-threshold 235 plus a specified safety margin. In another example, the HBP pulse amplitude may be set to the S-threshold 234 plus a specified safety margin. In yet another example, the HBP pulse amplitude may be set to a level between the S-threshold 234 and the NS-threshold 235, or an average or other linear or nonlinear combinations of S-threshold 234 and the NS-threshold 235.

In some examples, the parameter adjuster circuit 237 may determine the HBP pulse amplitude based on the S-threshold 234 relative to the NS-threshold 235. For example, the HBP pulse amplitude may be set to the S-threshold 234 plus a safety margin δ if the NS-threshold 235 and the S-threshold 234 are separated by a gap Δ greater than the safety margin δ (that is, δ<NS-threshold−S-threshold=Δ). Because such a pulse amplitude is above the S-threshold but still below the NS-threshold (that is, S-threshold+δ<NS-threshold), the HBP pulses are more likely to produce S-captures. Consequently, more physiological activation through the His-Purkinje system may result, and the energy-saving benefits associated with S-capture may also be achieved. If, however, the NS-threshold 235 and the S-threshold 234 are close enough to each such that the gap Δ between the two is less than the safety margin δ (that is, NS-threshold−S-threshold<δ), then the HBP pulse amplitude may be set to NS-threshold plus a specified safety margin δ. Because such a pulse amplitude exceeds the NS-threshold (that is, S-threshold+δ>NS-threshold), the HBP pulses are more likely to produce NS-captures. Although not as energy-efficient as selective HBP (i.e., HBP with S-capture), non-selective HBP (i.e., HBP with NS-capture) is less prone to LOC. Non-selective HBP may also be therapeutically as effective as selective HBP because the ventricular activation and contraction during NS-capture is vastly dominated by the majority of the ventricular myocardium activated by the His-Purkinje system.

As previously discussed, some patients may be suitable for selective HBP therapy, while some other patients may be suitable for non-selective HBP therapy. For a patient, the parameter adjuster circuit 237 may program the stimulation strength in accordance with the HBP thresholds (e.g., S-threshold or NS-threshold) to attain a desirable capture status (e.g., S-capture for selective HBP and NS-capture for non-selective HBP). However, HBP thresholds, after being generated, may change over time, such as due to changes in patient pathophysiology, medication, or lead migration or dislodgment. To maintain the desired capture status, the parameter adjuster circuit 237 may dynamically adjust stimulation strength, and the threshold test circuit 233 may accordingly update the HBP thresholds. In an example, if selective HBP is desired for a patient, then the parameter adjuster circuit 237 may set the stimulation strength above the determined S-threshold and below the determined NS-threshold. Over time, HBP at the programmed stimulation strength may produce consistent S-captures or LOCs, rather than desired NS-captures. A migration from S-capture to NS-capture may indicate a decrease in the previously determined NS-threshold. To maintain S-capture, the parameter adjuster circuit 237 may decrement stimulation strength until an S-capture status is detected; and the threshold test circuit 233 may accordingly update the NS-threshold with a new one corresponding to the S-capture detection. On the other hand, a migration from S-capture to LOC may indicate an increase in the previously determined S-threshold. To maintain S-capture, the parameter adjuster circuit 237 may increment stimulation strength until an S-capture is detected; and the threshold test circuit 233 may accordingly update the S-threshold with a new one corresponding to the S-capture detection.

In another example, if non-selective HBP is desired for a patient, then the parameter adjuster circuit 237 may set the stimulation strength above the determined NS-threshold. Over time, HBP at the programmed stimulation strength may produce consistent S-captures, indicating the NS-threshold has increased over time. To maintain NS-capture, the parameter adjuster circuit 237 may increment the stimulation strength until an NS-capture status is detected; and the threshold test circuit 233 may accordingly update the NS-threshold with a new one corresponding to the NS-capture detection.

In addition to the stimulation strength, the parameter adjuster circuit 237 may adjust one or more other stimulation parameters to more effectively activate the His-Purkinje system. In an example, the parameter adjuster circuit 237 may adjust stimulation site, such as by switching to a different stimulation vector configuration including an electrode in close proximity to the His bundle to improve the likelihood of selectively capturing the His-bundle. In another example, the parameter adjuster circuit 237 may adjust stimulation timing, such as an atrio-Hisian timing relative to an intrinsic or paced atrial event. In yet another example, the parameter adjuster circuit 237 may adjust stimulation mode, such as switching from AH mode to HV mode when a patient develops persistent or chronic atrial fibrillation, or treated with atrioventricular node ablation, or switch from AH pacing mode to AHV mode when the patient develops bundle branch block.

The stimulation control circuit 236 may additionally include a timing circuit 238 configured to time the delivery of the HBP pulses according to a stimulation timing parameter, such as an adjusted stimulation timing provided by the parameter adjuster circuit 237 or programmed by a user via a user interface 240. In an example, the timing circuit 238 may time the delivery of an HBP pulse using an atrio-Hisian (AH) window. The AH window is a programmable latency period with respect to an intrinsic (As) or paced atrial event (Ap). In an example, the AH window may be programmed to approximately 50 msec shorter than a sensed P wave-to-R wave (PR) interval or a programmed atrial-to-ventricular (AV) delay within a cardiac cycle. If an intrinsic His-bundle activity (Hs) is sensed within the AH window, the timing circuit 238 may initiate a His refractory period, during which an HBP pulse may be delivered. In another example, the AH window maybe determined based on an intrinsic AH interval, such that the AH window may be programmed to slightly longer than the intrinsic AH interval (e.g., approximately 1-30 msec longer than the intrinsic AH interval). The HBP would then be timed off a sensed atrial event but would occur just after the anticipated His event. The delivery of the HBP pulse may trigger a His capture verification window during which an evoked response, such as a FF-QRS or FF-R wave or a hemodynamic signal may be sensed.

In an example, a system user may program an AV delay and an HV interval, such that that AH timing may be determined as AH=AV−HV. The HV interval may be programmed to approximately 50-80 msec, which determines how far in advance to the end of the AV delay that the HBP pulse is delivered. The AV delay may be a sensed AV delay between an As event and a ventricular pacing pulse in the same cardiac cycle, or a paced AV delay between an Ap event and a ventricular pacing pulse in the same cardiac cycle. The paced AV delay may be programmed to be a slightly longer to allow for atrial pace latency and intra-atrial conduction delay.

The user interface 240 may include an input unit and an output unit. In an example, at least a portion of the user interface 240 may be implemented in the external system 140. The input unit may receive user input such as values of the parameters for physiologic event sensing, and His bundle response and myocardial response detections. The user input may receive user programming of stimulation parameters, or confirmation, rejection, or otherwise modification of the stimulation parameters generated by the parameter adjuster circuit 237. The input unit may include an input device such as a keyboard, on-screen keyboard, mouse, trackball, touchpad, touch-screen, or other pointing or navigating devices. The output unit may include circuitry configured to generate a human-perceptible notification of His-bundle capture status and/or various HBP thresholds. The output circuit may be coupled to a display for displaying the received physiologic signals, including tracings of one or more of atrial EGM, His-bundle EGM, ventricular EGM, surface electrocardiogram, or other sensor signals. The display may also display event sensing information such as intrinsic depolarizations, paced events (such as HBP pulses), and timing information on each of the sensed signals. The event sensing information may be overlaid with the signal tracings, or be displayed in a separate marker channel. The stimulation parameters, and intermediate measurements or computations may also be displayed. The output circuit 230 may be coupled to a printer for printing hard copies of information about the event detection and therapy titration protocol. The information may be presented in a table, a chart, a diagram, or any other types of textual, tabular, or graphical presentation formats. The presentation of the output information may include audio or other media formats. In an example, the output unit may generate alerts, alarms, emergency calls, or other forms of warnings to signal the system user about the His-bundle capture status. In an example, the output unit may generate an alert when a loss of capture is indicated and a backup pacing is delivered. In another example, frequent backup pacing delivery may trigger the output unit to generate an alert and prompt a user (e.g., a clinician) to reprogram the pacing system.

Figure 3:
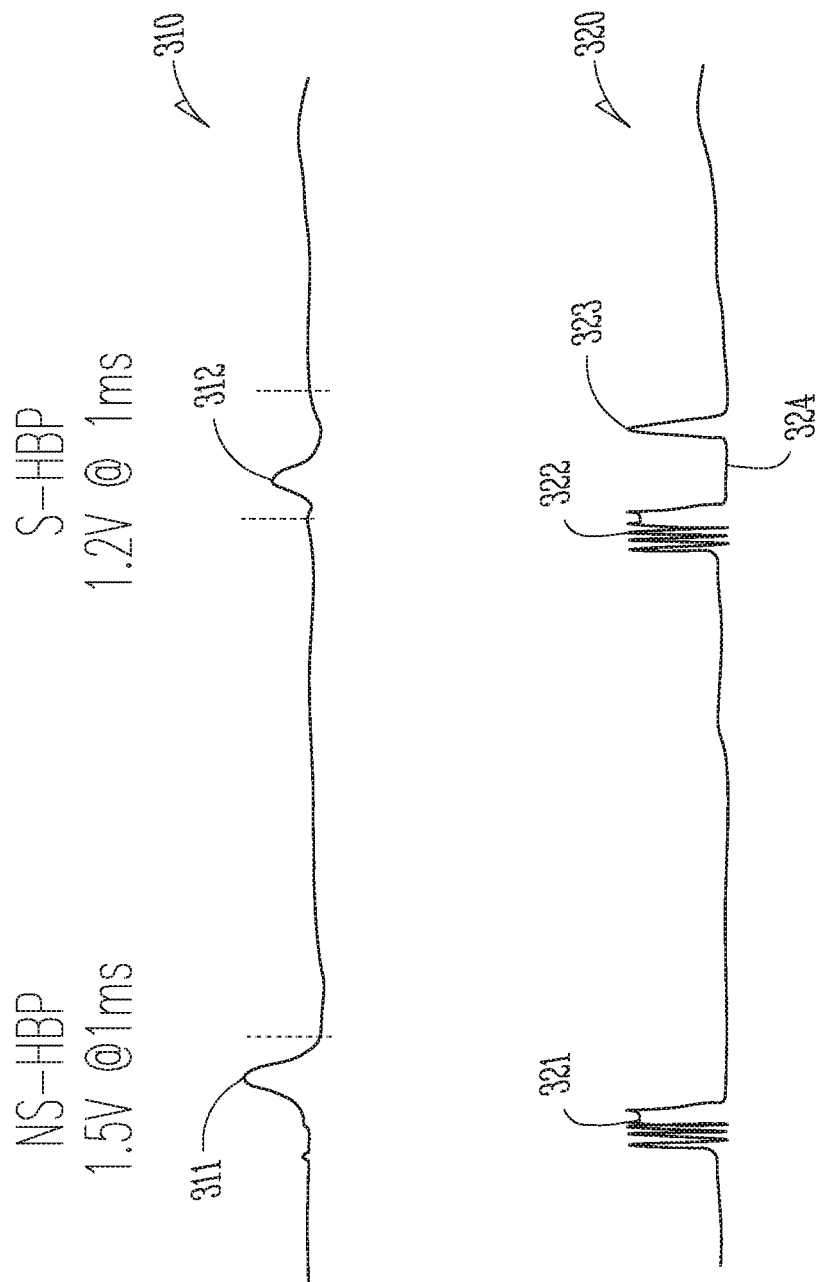
FIG. 3 illustrates examples of cardiac electrical signals recorded during an S-capture and a NS-capture.

FIG. 3 illustrates generally an example of cardiac electrical signals representing an S-capture and a NS-capture, including an ECG 310 recorded using surface electrodes, and a His-bundle EGM 320 recorded using His-bundle electrodes such as electrodes 112A-112B. An HBP pulse train having a pulse amplitude of 1.5V a pulse width of 1-msec produces a QRS complex 311 on the ECG 310. This HBP pulse train, represented by pacing artifact 321 on the His-bundle EGM 320, does not produce a local His-bundle activation. Based at least on the absence of a local His-bundle activation discrete from the pacing artifact, the capture verification circuit 232 may determine that an NS-capture has occurred. A second HBP pulse train having a lower pulse amplitude of 1.2V a pulse width of 1-msec produces a QRS complex 312 on the ECG 310. This HBP pulse train, represented by pacing artifact 322, also produces a local His-bundle activation 323 on the His-bundle EGM 320. The local His-bundle activation 323 is discrete from the pacing artifact 322, separated by an isoelectric interval 324. Based at least on the presence of a local His-bundle activation 323, and optionally together with the presence of isoelectric interval 324, the capture verification circuit 232 may determine that in this case an S-capture has occurred.

Detection of isoelectric interval 324 may be affected by factors such as configurations of stimulation electrodes and cardiac sensing electrodes. When cardiac pacing and cardiac sensing circuitry are coupled to separate electrodes (i.e., no common electrode used for both pacing and sensing), the isoelectric interval 324 may more likely to be detected. However, in some cases where the pacing and sensing circuitry share an electrode, the isoelectric interval 324 may not be detected in the presence of the pacing artifact 322. In such cases, the local His-bundle activation 323 may be superimposed on the pacing artifact 322. To detect the local His-bundle activation 323 in the presence of the pacing artifact, the sensing circuit 220 may be detect the local His-bundle activation 323 within a specified window. Methods of threshold test when a cathode is shared between cardiac stimulation vector and cardiac activation sensing vector, such as described by commonly assigned U.S. Pat. No. 8,688,216, entitled "AUTOTHRESHOLD WITH SENSING FROM PACING CATHODE", are herein incorporated by reference in its entirety.

Figure 4:
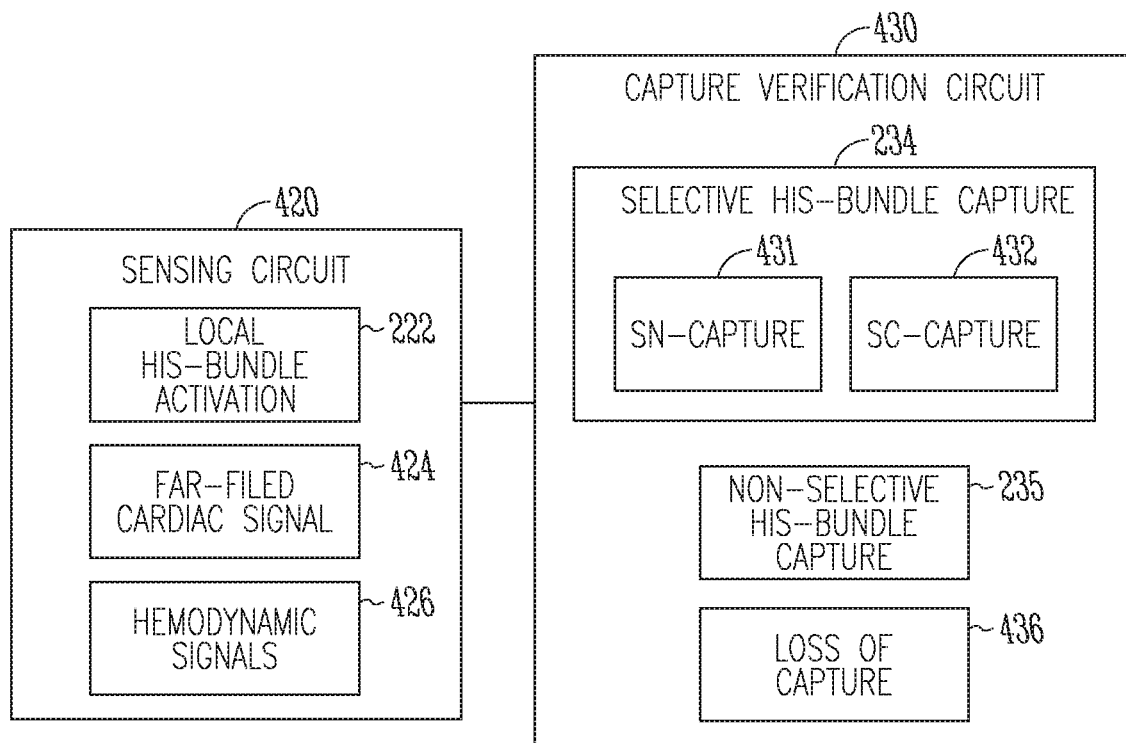
FIG. 4 is a block diagram illustrating an example of a capture verification circuit.

FIG. 4 illustrates generally an example of a capture verification circuit 430, which is an embodiment of the capture verification circuit 232. The capture verification circuit 430 may be coupled to a sensing circuit 420, which represents an embodiment of the sensing circuit 220. The sensing circuit 420 may sense one or more signal types or patient information including, by way of example and not limitation, local His-bundle activation 222, far-field (FF) cardiac signal 424, and hemodynamic signals 426. The FF cardiac signal 424 may include far-field QRS (FF-QRS) or far-field R-wave (FF-R) sensed at or near the His bundle or in an atrium. The FF cardiac signal 424 may include a bipolar EGM sensed using two electrodes disposed at or near the His bundle or in an atrium, or a unipolar EGM sensed between an electrode disposed at or near the His bundle or in an atrium and a reference electrode such as the housing 116 of the IMD 104. In some examples, an array of electrodes on the housing 116 may be electrically connected to increase the area of electrode-tissue interface. The capture verification circuit 430 may determine a capture status using timing information of a FF-QRS or FF-R wave. In an example, the capture verification circuit 430 may measure a time interval (HV interval) between an HBP pulse and a FF-QRS or FF-R wave. Generally, His-bundle capture (e.g., S-capture) may be characterized by a short HV interval due to faster propagation of the His-bundle depolarization through the His-Purkinje system. Para-Hisian capture or NS-capture may have relatively longer HV interval due to relatively slower, muscle-to-muscle conduction of the depolarization.

Additionally or alternatively, the capture verification circuit 430 may determine a capture status using morphology of a FF-QRS or FF-R wave. Due to the different conduction pathways involved and different conduction properties (e.g., velocity), His-bundle capture and para-Hisian myocardial capture may demonstrate different FF signal morphologies. The capture verification circuit 430 may extract from the FF cardiac signal 424 one or more FF morphological features, such as an R wave width, a slope of the upstroke or down-stroke branch of the R wave, or an area under the curve of the FF-QRS or FF-R wave, among others. In an example, an S-capture may be determined if a narrower FF-QRS or FF-R wave is detected. When only the para-Hisian myocardium is activated (e.g., para-Hisian capture), a wider FF-QRS or FF-R wave may result due to relatively slower, muscle-to-muscle conduction, and less coordinated contraction of the ventricles. A width threshold may be used to distinguish S-capture from capture of para-Hisian myocardium. In an example, the width threshold is approximately 90-120 msec. In an example, the width threshold may be at least partially automatically determined and dynamically updated based on patient historical HBP capture data.

HBP with different capture status may produce different hemodynamic outcome. The capture verification circuit 430 may detect from the hemodynamic signals 426 an increase in myocardial contractility in response to the delivery of the HBP pulses. In an example, a pressure sensor is configured to sense cardiac pressure. The capture verification circuit 430 may detect the increase in myocardial contractility based on a rate of increase in the cardiac pressure. In another example, an impendence sensor is configured to sense cardiac impedance. The capture verification circuit 430 may detect the increase in myocardial contractility based on a rate of increase in the cardiac impedance. The cardiac impedance may be measured by delivering high frequency subthreshold stimulation pulses, such as at approximately 20 Hz in an example. In an example, a volume plethysmography may be used to estimate cardiac contractility. In yet another example, a heart sound sensor is configured to sense heart sounds. The heart sound sensor may take the form of an accelerometer, an acoustic sensor, a microphone, a piezo-based sensor, or other vibrational or acoustic sensors. The accelerometer can be a two-axis or a three-axis accelerometer. Examples of the accelerometer may include flexible piezoelectric crystal (e.g., quartz) accelerometer or capacitive accelerometer, fabricated using micro electro-mechanical systems (MEMS) technology. One or more heart sound component, such as a first (S1), second (S2), third (S3), or fourth (S4) heart sound, may be detected from the heart sound signal. The hemodynamic sensor-based capture detector 320 may detect the increase in myocardial contractility based on a rate of increase in an intensity of the at least one heart sound component, or based on a rate of change in one or more HS-based cardiac timing intervals, such as a pre-ejection period (PEP), a systolic timing interval (STI), or a left-ventricular ejection time (LVET), among others. The detected increase in myocardial contractility may be compared to a threshold. A His-bundle capture is deemed to have occurred if the detected increase in myocardial contractility exceeds the threshold. Zhu et al. U.S. Pat. No. 8,688,234, entitled "DEVICES, METHODS, AND SYSTEMS INCLUDING CARDIAC PACING," refers to determining the effectiveness or completeness of His-bundle capture using attributes of a QRS signal, such as QRS narrowing, or using mechanical or hemodynamic sensors, which is incorporated herein by reference in its entirety. Dong et al. U.S. Pat. No. 8,565,880 entitled "HIS-BUNDLE CAPTURE VERIFICATION AND MONITORING," refers to His-bundle capture verification using hemodynamic sensors such as heart sound or blood pressure sensors, which is incorporated by reference herein in its entirety.

The capture verification circuit 430 may use one or more of the sensed signals or patient information to determine a HBP capture status, such as a selective His-bundle capture (S-capture) status 234, a non-selective His-bundle capture (NS-capture) status 235, or a loss of capture (LOC) status 436. In various examples, the capture verification circuit 430 may further recognize capture status associated with conduction abnormality, such as bundle branch block (BBB). The block can be located within the His bundle. Under the theory of longitudinal dissociation, fibers within the His bundle are separated from each other by encircling layers of collagen insulation and are pre-destined for their respective bundles. HBP pulses applied distal to the block but proximal to the bifurcation of the bundles, when programmed properly (e.g., having stimulation strength exceeding a threshold value), may bypass or overcome a structural block by recruiting previously latent conduction fibers in the His bundle, restore the natural conduction, and produce global myocardial activation through the His-Purkinje system. This is known as correction of His-Purkinje conduction abnormality. Such BP pulses, when programmed properly (e.g., having stimulation strength exceeding a threshold value), may additionally or alternatively correct the conduction abnormality by recruiting the latent conduction fibers and overcoming a functional block in local propagation.

By way of example and not limitation, FIG. 4 illustrates an S-capture without conduction abnormality correction ("Sn-capture") 431 and an S-capture with conduction abnormality correction ("Sc-capture") 432. For patients with left- or right-bundle branch block, HBP pulses with pulse amplitude above the S-threshold 234 may recruit a portion of the viable His-bundle system (e.g., right bundle), with some other portion (e.g., left bundle) being structurally or functionally blocked and thus not conducting distally to the Purkinje fibers. This HBP capture status is referred to as the Sn-capture. In these patients, further increasing the stimulation strength of HBP pulses may recruit previously latent His-bundle fibers (e.g., left bundle), resulting in Sc-capture, a type of S-capture associated with correction of conduction abnormality.

In various examples, the capture verification circuit 430 may distinguish an Sn-capture 431 from an Sc-capture 432 using a local His-bundle activation, such as the activation 323 detected from a His-bundle EGM 320 shown in FIG. 3, along with a far-field (FF) cardiac signal 424. Correction of conduction abnormality may cause changes in timing and/or morphology of FF cardiac signals 424. In an example, the capture verification circuit 232 may compare a FF-QRS or FF-R width, measured from the FF cardiac signals 424, to a specific threshold. If the FF-QRS or FF-R wave width falls below the specific threshold, a conduction abnormality may have been corrected, resulting in faster conduction through the His-Purkinje system and therefore a narrower QRS or R wave. Conversely, if the FF-QRS or FF-R wave width exceeds the specific threshold, then it is likely that no correction of conduction abnormality has occurred, corresponding to a wider QRS or R wave. Systems and methods for determining capture and particularly intra-Hisian block correction, such as described by commonly assigned U.S. Provisional Patent Application Ser. No. 62/595,541, entitled "SYSTEMS AND METHODS FOR CORRECTING CARDIAC CONDUCTION ABNORMALITY USING HIS-BUNDLE PACING", filed on Dec. 6, 2017, are herein incorporated by reference in its entirety.

Figure 5:
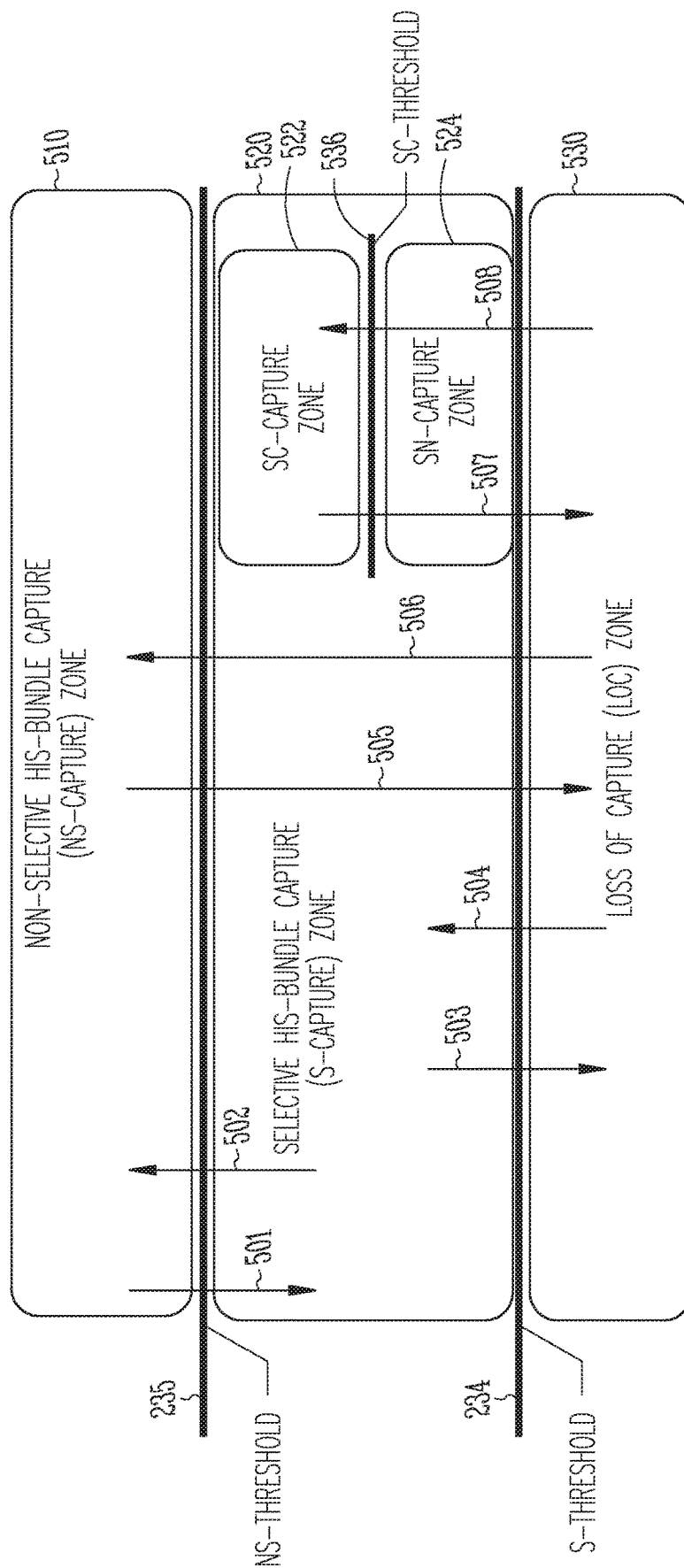
FIG. 5 is schematic diagram illustrating various threshold test protocols for determining one or more HBP thresholds.

FIG. 5 is schematic diagram illustrating various threshold test protocols 501-508 for determining one or more HBP thresholds. These test protocols may each be implemented in and executed by the threshold test circuit 233, or by a microprocessor. Test protocols 501-506 may be used to determine one or more of the S-threshold 234 and the NS-threshold 235. As previously discussed, energy required to activate only the His-bundle fibers is generally lower than energy required to activate both the His-bundle fibers and adjacent para-Hisian myocardium. Accordingly, the S-threshold 234 may be lower than the NS-threshold 235 in a patient.

As illustrated in FIG. 5, the S-threshold 234 and the NS-threshold 235 schematically divide an HBP capture status space into an NS-capture zone 510, an S-capture zone 520, and a loss of capture (LOC) zone 530. HBP pulses having stimulation strength higher than the NS-threshold 235 may produce NS-captures. HBP pulses having stimulation strength between the NS-threshold 235 and the S-threshold 234 may produce S-captures. HBP pulses having stimulation strength below the S-threshold 234 are likely to capture neither the His-bundle fibers nor the para-Hisian myocardium, resulting in LOCs.

Test protocol 501 represents graphically a ramp-down test to determine the NS-threshold 235. The test protocol 501 begins by delivering HBP pulses programmed with sufficiently high initial stimulation strength (e.g., pulse amplitude) to activate both the His-bundle fibers and the adjacent para-Hisian myocardium, that is, to produce NS-capture. The initial pulse amplitude may be determined empirically based on the pacing history date of the patient, or based on data from a patient population. The stimulation strength is then decremented in a manner as specified in the ramp-down protocol 501, such as following a stepwise decrement. The capture verification circuit 232 may monitor tissue response and determine capture status for each decremented stimulation strength. When the capture verification circuit 232 detects a transition from NS-capture status to S-capture status, the NS-threshold 235 may be determined as the stimulation strength (e.g., pulse amplitude) that corresponds to the transition to S-capture status. The NS-capture to S-capture transition may be recognized when the local His-bundle activation 323 is detected for the first time during the ramp-down test, optionally accompanied by an isoelectric interval 324, as depicted in FIG. 3. In various examples, other signals or patient information, such as far-field cardiac signals and/or hemodynamic signals, may be used to confirm the NS-capture to S-capture transition. In some examples, additional HBP pulses with the same stimulation strength that first produces the S-capture during the ramp-down test may be delivered, and the NS-threshold 235 may be determined if S-captures are confirmed with these additional HBP pulses.

Test protocol 502 represents graphically a ramp-up test to determine the NS-threshold 235, which represents a "reversed" version of the test protocol 501. The test protocol 502 begins by delivering HBP pulses programmed with stimulation strength (e.g., pulse amplitude) to activate only the His-bundle fibers but not para-Hisian myocardium, that is, to elicit S-capture. The initial pulse amplitude may be determined empirically based on the pacing history date of the patient, or based on data from a patient population. The stimulation strength is then incremented in a manner as specified in the ramp-up protocol 502, such as following a stepwise increment. The capture verification circuit 232 may monitor the tissue response, and detect a transition from S-capture status to NS-capture status (such as based on disappearance of the local His-bundle activation 323) for the first time during the ramp-up protocol. The threshold test circuit 233 may determine the NS-threshold 235 to be the stimulation strength corresponding to the detected transition.

Test protocol 503 represents graphically a ramp-down test to determine the S-threshold 234. The test protocol 503 begins by delivering HBP pulses programmed with certain stimulation strength (e.g., pulse amplitude) to activate only the His-bundle fibers, that is, to elicit S-capture. The stimulation strength is then decremented in a manner as specified in the ramp-down protocol 503, such as following a stepwise decrement. The capture verification circuit 232 may monitor the tissue response, and determine capture status for each decremented stimulation strength. When the capture verification circuit 232 detects a transition from S-capture status to LOC status (such as based on disappearance of the local His-bundle activation 323) for the first time during the ramp-down protocol, S-threshold 234 is deemed detected, by the threshold test circuit 233.

Test protocol 504 represents graphically a ramp-up test to determine the S-threshold 234, which represents a "reversed" version of the test protocol 503. The test protocol 504 begins by delivering HBP pulses programmed with sufficiently low initial stimulation strength (e.g., pulse amplitude) eliciting neither the His-bundle fibers nor the para-Hisian myocardium. The initial pulse amplitude may be determined empirically based on the pacing history date of the patient, or based on data from a patient population. The stimulation strength is then incremented in a manner as specified in the ramp-up protocol 504, such as following a stepwise increment. When the capture verification circuit 232 detects a transition from LOC to S-capture status (such as based on a detection of the local His-bundle activation 323) for the first time during the ramp-up protocol, the S-threshold 234 is deemed detected.

Test protocol 505 represents graphically a ramp-down test to determine sequentially the NS-threshold 235 and the S-threshold 234. The test protocol 505 combines the test protocols 501 and 503. Following a similar process to the protocol 501, the NS-threshold 235 may be determined based on a detection of a transition from NS-capture status to S-capture status. Subsequently, a similar process to the protocol 503 is followed to determine the S-threshold 234 based on a detection of a transition from S-capture status to LOC status.

Test protocol 506 represents graphically a ramp-up test to determine sequentially the S-threshold 234 and the NS-threshold 235. As illustrated, the test protocol 506 combines the test protocols 504 and 502, and represents a "reversed" version of the test protocol 505. Following a similar process to the protocol 504, the S-threshold 234 may be determined based on a detection of a transition from LOC status to S-capture status. Subsequently, a similar process to the protocol 502 is followed to determine the NS-threshold 235 based on a detection of a transition from S-capture status to NS-capture status. At least in some patients, it is relatively easier to determine a low initial stimulation strength for LOC status, or a high initial stimulation strength to ensure NS-capture status, than to determine an initial stimulation strength that may result in a S-capture. For these patients, test protocols 505 and 506 may be preferred over the test protocol 502 or 503 in some cases to determine the HBP thresholds.

Test protocols 507-508 may each be used to determine a selective HBP threshold with conduction abnormality correction (Sc-threshold) 536, which represents minimum energy (e.g., pulse amplitude) required to for HBP pulses to correct the conduction abnormality and produce Sc-capture. As discussed above with reference to FIG. 4, energy required to correct a conduction abnormality and produce an Sc-capture is generally higher than energy required to for an Sn-capture without conduction abnormality correction. As illustrated in FIG. 5, the Sc-threshold 536 divides the S-capture zone into an Sc-capture zone 522 and an Sn-capture zone 524.

According to the test protocol 507, HBP may be programmed initially to have stimulation strength sufficient to produce NS-capture, or an Sc-capture with a narrow FF-QRS or FF-R wave indicative of correction of conduction abnormality. By ramping down the stimulation strength, such as following a stepwise decrement, the capture verification circuit 232 may monitor the capture status, and detect a transition from Sc-capture to Sn-capture status (such as based on widening of FF-QRS or FF-R wave exceeding a threshold value), with preserved local His-bundle activation 323. The detected widening of FF-QRS or FF-R wave may indicate that the His-bundle has become at least partially blocked, which is a characteristic of Sn-capture status. The threshold test circuit 233 may determine the Sc-threshold 536 to be the stimulation strength corresponding to the detected transition.

Test protocol 508 represents graphically a ramp-up test to determine the Sc-threshold 536, which represents a "reversed" version of the test protocol 507. The test protocol 508 begins by delivering HBP pulses programmed with low initial stimulation strength (e.g., pulse amplitude), such as one that would produce a LOC or an Sn-capture with a wide FF-QRS or FF-R wave indicating presence of conduction block. The stimulation strength is then incremented, such as following a stepwise increment. The capture verification circuit 232 may monitor the capture status, and detect a transition from Sn-capture to Sc-capture status (such as based on narrowing of FF-QRS or FF-R wave (e.g., falling below a threshold value), accompanied by preserved local His-bundle activation 323. The detected narrowing of FF-QRS or FF-R wave may indicate that His-bundle conduction block has been corrected, a characteristic of Sc-capture status. The threshold test circuit 233 may determine the Sc-threshold 536 to be the stimulation strength corresponding to the detected transition.

In various examples, one or more test protocols may be selected from the protocols 501-508 or variations thereof according to patient condition and/or stimulation lead and electrode location or configurations. For example, test protocols 507 and 508 may be selected if a patient has His-Purkinje conduction abnormalities. In various examples, any of the test protocols 501-508 may be combined to determine one or more of the S-threshold 234, the NS-threshold 235, and the Sc-threshold 536. For example, the test protocols 505 and 507 may be combined to determine all of the S-threshold 234, the NS-threshold 235, and the Sc-threshold 536 in one combined test. Similarly, the test protocols 506 and 508 may be combined to determine all of the S-threshold 234, the NS-threshold 235, and the Sc-threshold 536 in one combined test.

In some examples, the parameter adjuster circuit 237 may use any of the threshold test protocol 501-508 or variations thereof to dynamically update an existing HBP threshold during the HBP therapy. In various examples, an absence of local His-bundle activation may indicate either an NS-capture such as due to a high stimulation strength above the NS-threshold 235, or a loss of capture such as due to a low stimulation strength below the S-threshold 234. To differentiate NS-capture from the LOC, the parameter adjuster circuit 237 may execute a ramp-down protocol to decrement pulse amplitude. The capture verification circuit 232 monitors capture status. If local His-bundle activation is detected for the first time during the ramp-down, it indicates a transition from NS-capture to S-capture has occurred. The parameter adjuster circuit 237 may determine a new NS-threshold corresponding to the detected transition from NS-capture to S-capture. If the ramp-down protocol does not result in a detection of local His-bundle activation after the pulse amplitude has been decremented to below a specified level, then it indicates LOC has occurred (as opposed to NS-capture). The parameter adjuster circuit 237 may then execute a ramp-up protocol to increment pulse amplitude. The capture verification circuit 232 monitors capture status, until it detects a local His-bundle activation. The parameter adjuster circuit 237 may determine a new S-threshold corresponding to the detected transition from LOC to S-capture.

Figure 6:
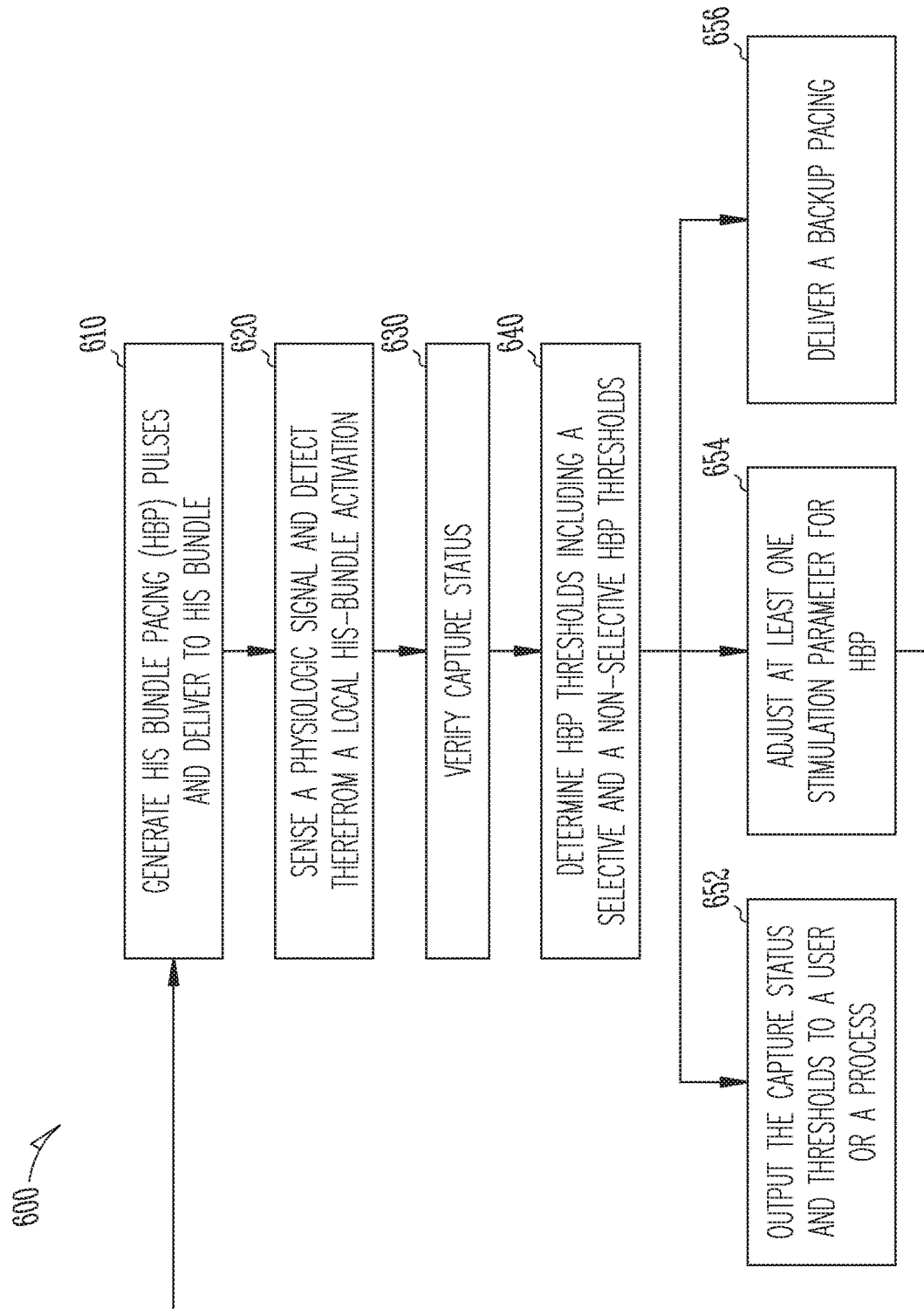
FIG. 6 is a flowchart illustrating generally an example of a method for providing HBP to a patient using a medical system.

FIG. 6 is a flowchart illustrating generally an example of a method 600 for providing His-bundle pacing (HBP) to a patient using a medical system. The method 600 may be implemented and executed in an ambulatory medical device such as an implantable or wearable medical device, or in a remote patient management system. In an example, the method 600 may be implemented in, and executed by, the IMD 104, one or more devices in the external system 140, or the His-bundle pacing system 200.

The method 600 commences at 610, where HBP pulses may be generated and delivered to a target site. The target site may include a region at or near the His bundle 121, such as a region distal to the blocked or slowly conducting AV node and in the AV septum, an interventricular septum region, or a right atrial region near the His-bundle 121. The HBP pulse may be generated by the electrostimulation circuit 210, according to programmed stimulation parameters. Examples of the stimulation parameters may include stimulation site, stimulation mode, stimulation timing, or stimulation strength, among other parameters. The stimulation strength parameters determine the amount of energy delivered to the pacing site, and may include pulse amplitude, pulse width, pulse frequency, pulse waveform, duty cycle, or stimulation duration. In an example, the HBP pulses may be programmed with different stimulation strength values, such as pulse amplitudes. The HBP pulses may be delivered via a delivery system including, for example, the lead 106 and one or more of the electrodes 112A-112B. In an example, HBP pulses may be delivered in multiple cardiac cycles, such that at least one pulse is delivered within each of the multiple cardiac cycles.

At 620, a physiologic signal may be sensed in response to the HBP pulses, such as using the sensing circuit 220. Examples of the sensed signals may include: an electrocardiogram (ECG); an electrogram of a portion of the heart such as atrial EGM, ventricular EGM, or evoked His potential; an impedance signal; a heart sound signal; or a pressure signal, among other physiological or hemodynamic signals indicative of a tissue response to the delivery of HBP pulses. A local His-bundle activation may be detected from the sensed physiologic signal. The local His-bundle activation is discrete from a pacing artifact of the HBP pulse, and may be detected in a detection time window that begins at the HBP pulse delivery, and sustains for a specified window duration. In an example, from a His-bundle EGM sensed using electrodes 112A or 112B, the local His-bundle activation may be detected based on EGM morphology. In various examples, an isoelectric interval preceding in time of the local His-bundle activation may be detected from the His-bundle EGM, as illustrated in FIG. 3. An isoelectric interval is a time interval between the pacing artifact of the HBP pulse and the local His-bundle activation, during which the EGM maintains a baseline level. Presence of the isoelectric interval may be determined by comparing the His-bundle EGM amplitude (e.g., between the artifact of the HBP pulse and the local His-bundle activation) to a threshold.

At 630, a capture status may be determined, such as by the capture verification circuit 232. The capture status represents types of tissue (e.g., His-bundle fibers, or myocardium at the stimulation site) directly activated by the HBP pulses and the manners of activation. The capture status may be verified on a beat-by-beat basis over multiple cardiac cycles. In an example, the capture status may be determined respectively for HBP pulses programmed with each of a number stimulation parameter values, such as pulse amplitudes.

Examples of capture status include a selective His-bundle capture (S-capture) status, a non-selective His-bundle capture (NS-capture) status, a para-Hisian capture status, or a loss of capture (LOC) status, among others. An S-capture occurs if the HBP activates only the His bundle without directly activating the adjacent working myocardium. An NS-capture occurs if the His-bundle pacing directly activates both the His bundle and the adjacent working myocardium. A para-Hisian capture status results if the HBP pulses cause only activation of the para-Hisian myocardium or other un-intended cardiac tissue, without substantial activation of the His bundle directly caused by the pacing pulses. An LOC occurs if no tissue activation is induced by HBP.

Capture status may be determined based on the sensed local His-bundle activation, or optionally further based on the isoelectric interval. In an example, an S-capture status is determined if the local His-bundle activation is present, and an NS-capture status is determined if the local His-bundle activation is absent. Additionally, presence of the isoelectric interval may be indicative of S-capture, while absence of the isoelectric interval may be indicative of NS-capture, likely due to ventricular fusion and pseudo-delta wave subsequent to the HBP pacing artifact, as illustrated in FIG. 3. In various examples, the capture status may be determined using additional patient information, such as far-field cardiac electrical signals and/or patient hemodynamic information, as to be discussed with reference to FIG. 7.

In some examples, at 630, a partial capture status may be determined. A partial capture refers to capture of a portion of the His-bundle fibers. In these patients, HBP may recruit a portion, but not all, of the viable His-bundle system, with other portions being structurally or functionally blocked and thus not conducting distally to the Purkinje fibers. In an example, capture occurs in one bundle branch (e.g., right bundle branch), and the other branch (e.g., left bundle branch) is structurally or functionally blocked. In another example, partial capture may occur within the His-bundle, or within a bundle branch. For example, within a left bundle branch, blockage is present in only a portion, but not all, of the fascicles. In this document, the partial His-bundle capture is also referred to as capture with non-correction of conduction abnormality (Sn-capture). Further increase of stimulation strength of HBP pulses may recruit previously latent His-bundle fibers (e.g., blocked bundle, or blocked portion within a bundle), resulting in Sc-capture that corrects the conduction abnormality.

At 640, one or more HBP thresholds may be determined using the detected capture status corresponding to HBP at various stimulation strength (e.g., pulse amplitudes), such as by the threshold test circuit 233. By way of example and not limitation, the HBP thresholds include an S-threshold representing minimum energy (e.g., pulse amplitude) required to produce an S-capture status by HBP, and an NS-threshold representing minimum energy (e.g., pulse amplitude) required to produce an NS-capture status by HBP. To determine the HBP thresholds such as S-threshold or NS-threshold, one or more threshold test protocols may be executed. According to a test protocol, stimulation strength (e.g., pulse amplitude) may be varied in a specific manner (e.g., ramping down, ramping up, or sweeping through a number of stimulation strength value), and capture status may be determined for each stimulation strength. A capture status transition from a first capture status to a second capture status of a different type may be detected as the pulse amplitude varies according to the test protocol. FIG. 5 illustrates examples of HBP threshold test protocols, which may be used for determining one or more of the S-threshold, the NS-threshold, or an HBP threshold associated with conduction abnormality correction, such as the selective HBP threshold with conduction abnormality correction (Sc-threshold) representing minimum energy (e.g., pulse amplitude) required to for HBP pulses to correct the conduction abnormality and produce Sc-capture. As illustrated in FIG. 5, the NS-threshold schematically divides the NS-capture zone and the S-capture zone, and the S-threshold schematically divide the NS-capture zone and the LOC zone. An NS-threshold may be determined by executing a threshold test protocol that would produce a transition between NS-capture and S-capture when delivering HBP by incrementally or detrimentally varying stimulation strength. An S-threshold may be determined by executing a threshold test protocol that would produce a transition between LOC and S-capture when delivering HBP by incrementally or detrimentally varying stimulation strength. Similarly, the Sc-threshold schematically divides the Sc-capture zone and the Sn-capture zone. An Sc-threshold may be determined by executing a threshold test protocol that would produce a transition between Sc-capture and Sn-capture when delivering HBP by incrementally or detrimentally varying stimulation strength.

The His-bundle capture status and the HBP thresholds may be output to a user (e.g., a clinician) or a process at 652, such as being displayed on a display of the user interface 240. The sensed physiologic signals, the detection results of local His-bundle activations such as those illustrated in FIG. 3, or the programmed stimulation parameters, among other intermediate measurements or computations, may also be displayed. Additionally or alternatively, at 654, one or more stimulation parameters may be adjusted such as via the parameter adjuster circuit 237. The parameter adjustment may include switching to a different stimulation site, using a different pacing vector configurations, adjusting the AH timing with respect to an intrinsic or paced atrial activation, adjusting stimulation strength such as one or more of pulse amplitude, pulse width, pulse frequency, pulse waveform, duty cycle, or stimulation duration. In some examples, stimulation parameter adjustment may be based on capture statistics computed using the capture verification and classification results over multiple heart beats. Examples of the capture statistics may include percentages, histograms, or other measures of distribution of the selective His-bundle capture, non-selective His-bundle capture, or para-Hisian capture.

The parameter adjusted may be based at least on the capture status and/or various HBP thresholds. For example, HBP pulse amplitude may be programmed to the NS-threshold plus a specified safety margin $\delta$, to the S-threshold 234 plus a specified safety margin $\delta$, an average of the S-threshold and the NS-threshold, or other value between the S-threshold and NS-threshold. In some examples, HBP pulse amplitude may be set to a value based on a comparison of the S-threshold and the NS-threshold. For example, the HBP pulse amplitude is set to the S-threshold plus a specified safety margin if the NS-threshold and the S-threshold are separated by a gap $\Delta$ greater than the safety margin $\delta$. If the gap $\Delta$ between the NS-threshold and the S-threshold is less than the safety margin $\delta$, then the HBP pulse amplitude is set to NS-threshold plus a safety margin $\delta$. In some examples, the pulse amplitude, among other stimulation parameters, may be adjusted dynamically during a HBP session to maintain a desirable capture status. For example, if S-capture is desired, then in response to NS-capture, the pulse amplitude may be decreased until an S-capture status is verified. If NS-capture is desired, then in response to a verification of a LOC, the pulse amplitude may be increased until an S-capture status is verified.

At 656, a backup pacing may be delivered when certain capture status results, such as a LOC, or a para-Hisian capture. The backup pacing may be delivered to a target ventricular site via a lead with associated electrodes disposed in or on a ventricle, such as a right ventricle. Additionally or alternatively, the backup pacing may be delivered at or near the His bundle. In an example, the backup pacing pulses include high-output pacing (HOP) pulses with higher pacing energy than conventional pacing pulses. In some examples, the HOP pulses may be delivered on an intermittent basis, such that the conventional pacing pulses are delivered in 3-5 cardiac cycles between the HOP pulses. In addition to backup ventricular pacing, other therapies, such as CRT, BiV pacing, LV-only pacing, single site LV pacing, or multi-site LV pacing may be delivered to improve myocardial contractility and cardiac performance.

Figure 7:
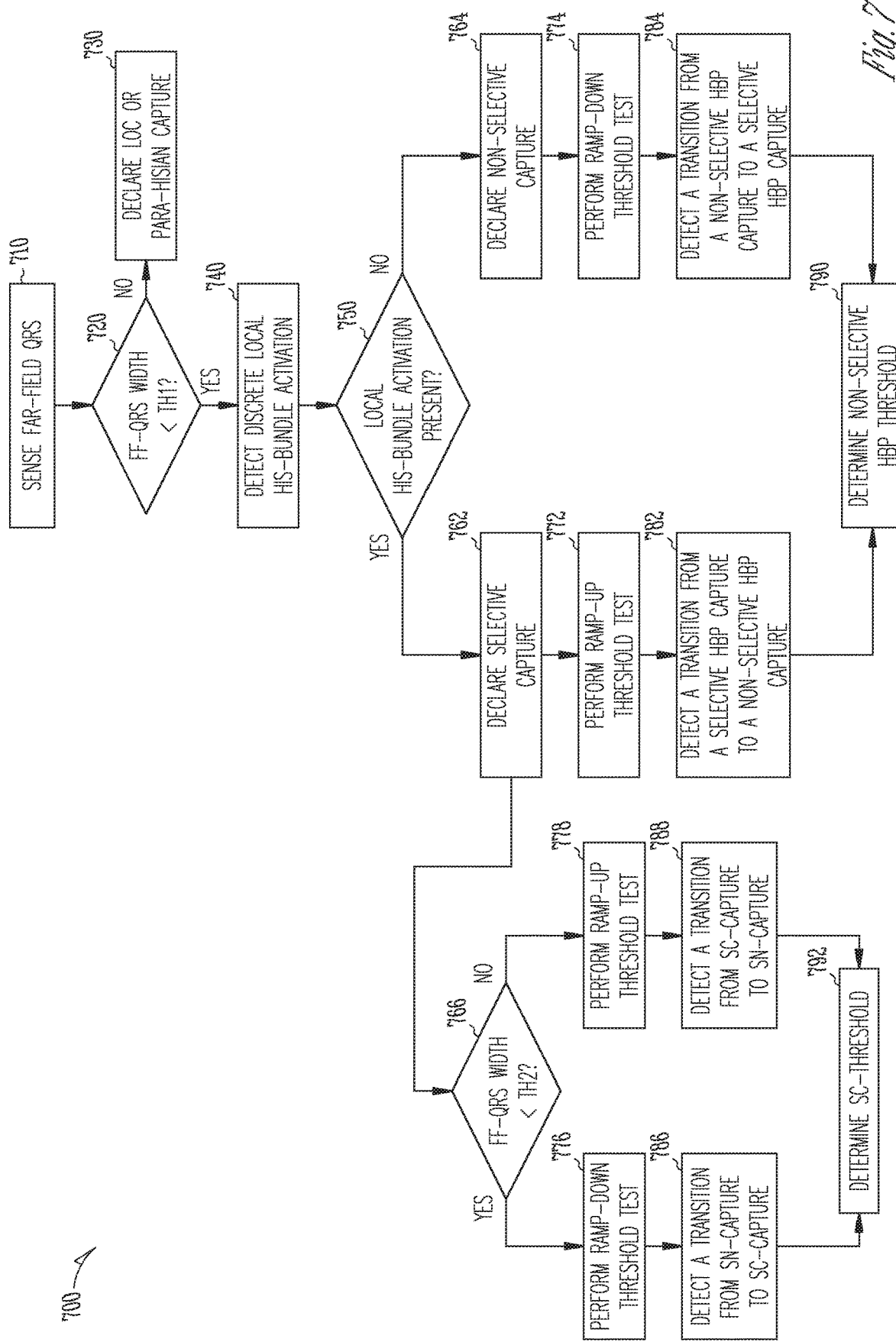
FIG. 7 is a flowchart illustrating generally a method for determining His-bundle capture status and HBP thresholds.

FIG. 7 is a flowchart illustrating generally a method 700 for determining His-bundle capture status and the HBP thresholds, such as an NS-threshold. The method 700 represents an embodiment of at least a portion, such as corresponding to steps 610-640, of the method 600. According to method 700, capture status, and NS-threshold, may be determined based on a local His-bundle activation and a far-field cardiac electrical signal. The method may be implemented and executed in an ambulatory medical device that includes a capture verification circuit 430, as illustrated in FIG. 4.

The method 700 commences at 710 to sense a far-field (FF) cardiac electrical signal representative of ventricular contractions, such as using electrodes disposed at or near the His bundle (e.g., one or more of the electrodes 112A and 112B), or electrodes disposed in an atrium. In an example, the FF cardiac signal may be sensed in response to HBP pulses delivered to multiple cardiac cycles, such that at least one pulse is delivered in each of the multiple cardiac cycles. By way of example and not limitation, the FF cardiac signal include far-field QRS (FF-QRS) or far-field R-wave (FF-R) extracted from a FF EGM sensed at the His bundle or an atrium.

Timing or morphological information may be extracted from the FF cardiac signal. At 720, a morphological feature, such as FF-QRS width, may be compared to a threshold (TH1). In an example, the threshold TH1 is approximately between 90-120 msec. Due to the different conduction pathways involved and different conduction properties (e.g., velocity), His-bundle capture and para-Hisian myocardial capture may demonstrate different FF signal morphologies. His-bundle capture (e.g., S-capture or NS-capture) may be characterized by a narrower FF-QRS or FF-R wave due to recruitment of fast conduction pathway and more coordinated contraction of the ventricles. When only para-Hisian myocardium is activated without (e.g., para-Hisian capture), a wider FF-QRS or FF-R wave may result due to relatively slower, muscle-to-muscle conduction, and less coordinated contraction of the ventricles. As illustrated in FIG. 7, if the FF-QRS width is greater than the threshold TH1, wide FF-QRS is indicated, and a para-Hisian or LOC is declared at 730. If the FF-QRS width is shorter than the threshold TH1, then narrow FF-QRS is indicated, and a discrete local His-bundle activation may be detected at 740, as discussed above with reference to step 620 of FIG. 6. If it is determined at 750 that a local His-bundle activation is present, or additionally an isoelectric interval is present, then an S-capture is declared at 762. A ramp-up threshold test may be carried out at 772, such as in accordance with the test protocol 502 as illustrated in FIG. 5. In particular, HBP pulses may be delivered with pulse amplitudes being incremented such as in a stepwise fashion, and capture status is monitored during the ramp-up of the pulse amplitude. At 782, a transition from S-capture to NS-capture may be detected, such as an absence of the local His-bundle activation for the first time during the ramp-up protocol. At 790, an NS-threshold may be determined as the pulse amplitude corresponding to the detected transition.

If at 750 it is determined that a local His-bundle activation is not present, then an NS-capture is declared at 764. A ramp-down threshold test may be carried out at 774, such as in accordance with the test protocol 501 as illustrated in FIG. 5. In particular, HBP pulses may be delivered with pulse amplitudes being decremented such as in a stepwise fashion, and capture status is monitored during the ramp-down of the pulse amplitude. At 784, a transition from NS-capture to S-capture may be detected, such as a presence of the local His-bundle activation, or additionally accompanied by an isoelectric interval, for the first time during the ramp-down protocol. At 790, an NS-threshold may be determined as the pulse amplitude corresponding to the detected transition.

In various examples, other signals or patient information, such as far-field cardiac signals and/or hemodynamic signals, may be used to confirm the S-capture detection at 762, or the NS-capture at 764. In some examples, at 782 (or similarly at 784), additional HBP pulses with the same stimulation strength that produces the capture status transition may be delivered, and the NS-threshold may be determined if NS-captures are consistently detected at 782 (or S-captures are consistently detected at 784) with these additional HBP pulses.

Although the method 700 focuses on a method of determining NS-threshold, this is meant only by way of example and not limitation. In various examples, the method 700 may be modified to alternatively or additionally determine other HBP thresholds, such as S-threshold or Sc-threshold. In an example, following an S-capture detection at 762, a ramp-down threshold test may be performed, such as in accordance with the test protocol 503. A transition from the S-capture to LOC may be detected, such that the local His-bundle activation become absent for the first time during the ramp-down protocol, or additionally accompanied by wide FF-QRS. An S-threshold may then be determined as the pulse amplitude corresponding to the detected transition. In another example, following a LOC declaration at 730, a ramp-up threshold test may be performed, such as in accordance with the test protocol 504. A transition from the LOC to S-capture may be detected, such as a narrow FF-QRS accompanied by a local His-bundle activation. An S-threshold may then be determined as the pulse amplitude corresponding to the detected transition.

In another example, the method 700 may be modified to determine Sc-threshold. Following an S-capture detection at 762, Sn-capture status or Sc-capture status may be determined, such as based on the FF-QRS width at 766. If the FF-QRS width is shorter than a threshold TH2, then a Sc-capture status is detected, and a ramp-down threshold test in accordance with the test protocol 507 may be performed at 776. The threshold TH2 at 766 may be smaller than the threshold TH1 at step 720. During the ramp-down test, the capture status is monitored, and a transition from Sc-capture to Sn-capture status may be detected at 786, such as based on widening of the FF-QRS wave exceeding the threshold TH2, while the local His-bundle activation remains to be present during the ramp-down test (or optionally accompanied by the presence of isoelectric interval). At 792, an Sc-threshold may then be determined as the pulse amplitude corresponding to the detected transition.

If at 763 the FF-QRS width is greater than the threshold TH2, then a Sn-capture status is detected; and a ramp-up threshold test in accordance with the test a ramp-up threshold test in accordance with the test protocol 508 may be performed at 778. During the ramp-up test, the capture status is monitored, and a transition from Sn-capture to Sc-capture status may be detected at 788, such as based on shortening of FF-QRS falling below the threshold TH2, while the local His-bundle activation remains to be present during the ramp-down test (optionally accompanied by the presence of isoelectric interval). An Sc-threshold may then be determined as the pulse amplitude corresponding to the detected transition.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for pacing a heart, comprising:
   an electrostimulation circuit configured to generate His-bundle pacing (HBP) pulses having a stimulation strength to stimulate a His bundle of the heart;
   a sensing circuit configured to sense a physiologic signal and to detect, from the sensed physiologic signal, a presence or absence of a local His-bundle activation discrete from a pacing artifact of the delivered HBP pulses and an isoelectric interval that separates the local His-bundle activation from the pacing artifact of the delivered HBP pulse; and
   a control circuit configured to:
      classify a capture status as being one of two or more different types of capture status based at least on the presence or absence of the local His-bundle activation and the detected isoelectric interval; and
      determine, using the classified capture status, one or more of (1) a selective HBP threshold (S-threshold) representing a threshold strength for the HBP pulses to capture only the His bundle but not local myocardium, or (2) a non-selective HBP threshold (NS-threshold) representing a threshold strength for the HBP pulses to capture both the His bundle and the local myocardium.

2. The system of claim 1, wherein the control circuit is configured to classify the capture status at a specific stimulation strength using a plurality of detected local His-bundle activations in response to a plurality of HBP pulses having the specific stimulation strength.

3. The system of claim 1, wherein the sensing circuit is configured to sense the physiologic signal including a His-bundle electrogram, and to detect the presence or absence of the local His-bundle activation using an amplitude or a morphology of the sensed His-bundle electrogram.

4. The system of claim 1, wherein the control circuit is configured to classify the capture status as one of:
   a selective His-bundle capture (S-capture) status if the local His-bundle activation is present, the S-capture status representing a capture of only the His bundle but not the local myocardium;
   a non-selective His-bundle capture (NS-capture) status if the local His-bundle activation is absent, the NS-capture status representing a capture of both the His bundle and the local myocardium; or
   a loss of capture (LOC) status indicative of a capture of neither the His bundle nor the local myocardium.

5. The system of claim 4, wherein the control circuit is configured to:
   detect a first transition from an S-capture status to an NS-capture status in response to HBP pulses delivered according to a ramp-up of the stimulation strength, or a second transition from an NS-capture status to an S-capture status in response to HBP pulses delivered according to a ramp-down of the stimulation strength; and
   determine the NS-threshold corresponding to the detected first or second transition of capture status.

6. The system of claim 4, wherein the control circuit is configured to:
   detect a third transition from an LOC status to an S-capture status in response to HBP pulses delivered according to a ramp-down of the stimulation strength, or a fourth transition from an S-capture status to an LOC status in response to HBP pulses delivered according to a ramp-down of the stimulation strength; and
   determine the S-threshold corresponding to the detected third or fourth transition of capture status.

7. The system of claim 1, wherein the control circuit is configured to:
   classify the capture status as one of (1) a selective His-bundle capture with conduction abnormality correction (Sc-capture), or (2) a selective His-bundle capture without conduction abnormality correction (Sn-capture); and
   determine a selective HBP threshold with conduction abnormality correction (Sc-threshold) based on at least the classification of the Sc-capture status or the Sn-capture status.

8. The system of claim 7, wherein the control circuit is configured to:
   ramp up the stimulation strength, and determine the Sc-threshold corresponding to a transition from an Sn-capture status to an Sc-capture status in response to HBP pulses delivered according to the ramp-up of the stimulation strength; or
   ramp down the stimulation strength, and determine the Sc-threshold corresponding to a transition from an Sc-capture status to an Sn-capture status in response to HBP pulses delivered according to the ramp-down of the stimulation strength.

9. The system of claim 4, wherein:
   the sensing circuit is further configured to sense a far-field cardiac electrical signal; and
   the control circuit is configured to classify the capture status further using the sensed far-field cardiac electrical signal.

10. The system of claim 9, wherein:
    the sensing circuit is configured to extract a morphologic feature of the far-field cardiac electrical signal; and
    the control circuit is configured to, in response to the extracted morphologic feature satisfying a specified condition, determine an NS-threshold corresponding to (1) a transition from an S-capture status to an NS-capture status in response to HBP pulses delivered according to a ramp-up of the stimulation strength, or (2) a transition from an NS-capture status to an S-capture status in response to HBP pulses delivered according to a ramp-down of the stimulation strength.

11. The system of claim 4, wherein:
    the electrostimulation circuit is configured to generate the HBP pulses having stimulation strength above the determined NS-threshold; and
    the control circuit is configured to, in response to an S-capture status, increment the stimulation strength until the capture status becomes an NS-capture status.

12. The system of claim 4, wherein:
    the electrostimulation circuit is configured to generate the HBP pulses having stimulation strength above the determined S-threshold and below the determined NS-threshold; and
    the control circuit is configured to:
    in response to an NS-capture status, decrement the stimulation strength until the capture status becomes an S-capture status; and
    in response to a loss of capture status, increment the stimulation strength until the capture status becomes an S-capture status.

13. A method for operating a pacing system to stimulate a heart, the method comprising:
- generating, via an electrostimulation circuit, His-bundle pacing (HBP) pulses to stimulate a His bundle of the heart, the HBP pulses having a stimulation strength;
- sensing, via a sensing circuit, a physiologic signal and determining a presence or absence of a local His-bundle activation discrete from a pacing artifact of the delivered HBP pulse;
- detecting an isoelectric interval that separates the local His-bundle activation from the pacing artifact of the delivered HBP pulse;
- classifying, via a control circuit, a capture status as being one of two or more different types of capture status based at least on the presence or absence of the local His-bundle activation and the detected isoelectric interval; and
- determining, using the classified capture status, one or more of a selective HBP threshold (S-threshold) or a non-selective HBP threshold (NS-threshold) via the control circuit, the S-threshold representing a threshold strength for the HBP pulses to capture only the His bundle but not local myocardium, the NS-threshold representing a threshold strength for the HBP pulses to capture both the His bundle and the local myocardium.

14. The method of claim 13, wherein classifying the capture status includes classifying the capture status as one of:
- a selective His-bundle capture (S-capture) status if the local His-bundle activation is present, the S-capture status representing a capture of only the His bundle but not the local myocardium;
- a non-selective His-bundle capture (NS-capture) status if the local His-bundle activation is absent, the NS-capture status representing a capture of both the His bundle and the local myocardium; or
- a loss of capture (LOC) status indicative of a capture of neither the His bundle nor the local myocardium.

15. The method of claim 13, further comprising:
- classifying the capture status as one of (1) a selective His-bundle capture with conduction abnormality correction (Sc-capture), or (2) a selective His-bundle capture without conduction abnormality correction (Sn-capture); and
- determining a selective HBP threshold with conduction abnormality correction (Sc-threshold) based on at least the classification of the Sc-capture status or the Sn-capture status.

16. The method of claim 15, wherein determining the Sc-threshold includes at least one of:
- ramping up the stimulation strength, and determining the Sc-threshold corresponding to a transition from an Sn-capture status to an Sc-capture status in response to HBP pulses delivered according to the ramp-up of the stimulation strength; or
- ramping down the stimulation strength, and determining the Sc-threshold corresponding to a transition from an Sc-capture status to an Sn-capture status in response to HBP pulses delivered according to the ramp-down of the stimulation strength.

17. The method of claim 13, comprising:
- sensing a far-field cardiac electrical signal;
- classifying the capture status further using the sensed far-field cardiac electrical signal; and
- in response to the far-field cardiac electrical signal satisfying a specified condition, determining an NS-threshold corresponding to (1) a transition from an S-capture status to an NS-capture status in response to HBP pulses delivered according to a ramp-up of the stimulation strength, or (2) a transition from an NS-capture status to an S-capture status in response to HBP pulses delivered according to a ramp-down of the stimulation strength.

18. A system for pacing a heart, comprising:
- an electrostimulation circuit configured to generate His-bundle pacing (HBP) pulses having a stimulation strength to stimulate a His bundle of the heart;
- a sensing circuit configured to sense a physiologic signal, and to detect, from the sensed physiologic signal, a presence or absence of a local His-bundle activation separated from a pacing artifact of the delivered HBP pulses by an isoelectric interval; and
- a control circuit configured to classify a capture status as being one of two or more different types of capture status based on the local His-bundle activation and the isoelectric interval that separates the local His-bundle activation and the pacing artifact.

19. The system of claim 18, wherein the control circuit is configured to classify the capture status as one of:
- a selective His-bundle capture (S-capture) status if the local His-bundle activation is present and the isoelectric interval is present, the S-capture status representing a capture of only the His bundle but not the local myocardium; or
- a non-selective His-bundle capture (NS-capture) status if the local His-bundle activation is absent or the isoelectric interval is absent, the NS-capture status representing a capture of both the His bundle and the local myocardium.

20. The system of claim 18, wherein the control circuit is configured to classify the capture status at a specific stimulation strength using a plurality of detected local His-bundle activations in response to a plurality of HBP pulses having the specific stimulation strength.

* * * * *